United States Patent [19]

Wentland

[11] Patent Number: 4,959,363

[45] Date of Patent: Sep. 25, 1990

[54] QUINOLONECARBOXAMIDE COMPOUNDS, THEIR PREPARATION AND USE AS ANTIVIRALS.

[75] Inventor: Mark P. Wentland, Colonie, N.Y.

[73] Assignee: Sterling Drug Inc., New York, N.Y.

[21] Appl. No.: 370,926

[22] Filed: Jun. 23, 1989

[51] Int. Cl.$^5$ ................ C07D 215/233; C07D 265/30; A61K 31/47; A61K 31/535
[52] U.S. Cl. .................... 514/235.2; 514/312; 544/128; 546/153; 546/155; 546/156
[58] Field of Search ........................ 546/153, 155, 156; 514/312, 235.2; 544/128

[56] References Cited

U.S. PATENT DOCUMENTS

| Re.32,975 | 7/1989 | Grobe et al. | 514/312 |
| 3,753,993 | 8/1973 | Lesher et al. | 260/286 |
| 3,966,743 | 6/1976 | Berger et al. | 546/156 |
| 4,499,091 | 2/1985 | Wentland et al. | 514/235.2 |
| 4,636,506 | 1/1987 | Gilligan et al. | 514/256 |
| 4,730,000 | 3/1988 | Chu | 514/254 |
| 4,786,644 | 11/1988 | Glamkowski et al. | 514/312 |

FOREIGN PATENT DOCUMENTS 0172004 2/1986 European Pat. Off. .
1433774 4/1976 United Kingdom .

OTHER PUBLICATIONS

Angelino et al., J. Heterocyclic Chem., 21, 107–112, (1984).

Primary Examiner—Mukund J. Shah
Assistant Examiner—E. C. Ward
Attorney, Agent, or Firm—Thomas L. Johnson; FrederiK W. Stonner; Paul E. Dupont

[57] ABSTRACT

Compounds of the formula

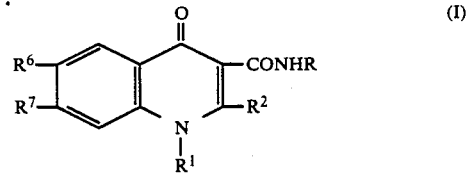

where R is hydrogen, hydroxy, amino or lwer-alkyl; $R^1$ is lower-alkyl, lower-alkenyl, cycloalkyl, pyridinyl, phenyl or substituted phenyl; $R^2$ is hydrogen, amino or hydroxy; $R^6$ is hydrogen or fluoro; and $R^7$ is phenyl, pyridinyl or selected other heterocycles, have antiviral acitivity against herpes virus.

The compounds are prepared from the corresponding carboxylic acids or ester, or by a tin-coupling reaction on the corresponding 7-halo compounds.

12 Claims, No Drawings

QUINOLONECARBOXAMIDE COMPOUNDS, THEIR PREPARATION AND USE AS ANTIVIRALS.

BACKGROUND OF THE INVENTION (a) Field of the Invention

This invention relates to novel 1,4-dihydro-4-oxo-3-quinolinecarboxamides, to methods for the preparation thereof, and compositions and methods for the use thereof as antiviral agents.

(b) Information Disclosure Statement 1,4-Dihydro-4-oxo-3-quinolinecarboxylic acids constitute a well-known class of compounds having antibacterial activity. They are, however, essentially devoid of antiviral activity. Representative acids in the prior art are the following:

1,4-Dihydro-1-ethyl-7-(4-pyridinyl)-4-oxo-3quinolinecarboxylic acid [Lesher et al. U.S. Pat. No. 3,753,993, issued August 21, 1973].

1,4-Dihydro-6,8-difluoro-1-ethyl-7-(4-pyridin-yl)-4-oxo-3-quinolinecarboxylic acid [Gilligan et al. U.S. Pat. No. 4,636,506, issued Jan. 13, 1987].

1,4-Dihydro-6-fluoro-1-(p-fluorophenyl)-4-oxo-7(1-piperazinyl)-3-quinolinecarboxylic acid [Chu U.S. Pat. No. 4,730,000, issued Mar. 8, 1988].

1,4-Dihydro-4-oxo-3-quinolinecarboxamides which are known in the art include the following: 1,4-Dihydro-1-methyl-4-oxo-3-quinolinecarboxamide [Angelino et al., J. Heterocyclic Chem. 21, 107 (1984)]. No utility is disclosed for the compound.

N-(1-Tetrazolyl)-1,4-dihydro-1-ethyl-7-(4-methyl-1-piperazinyl)-4-oxo-3-quinolinecarboxamide Allen and Hanburys Ltd. British Patent No. 1,433,774, granted Apr. 28, 1976]. The compounds of the patent are stated to be anti-allergic agents.

Boots Company European Patent Application Publ. No. 172004 (published 2-19-86) contemplates compounds of the formula

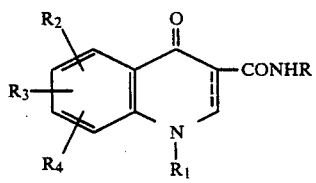

in which the dotted line between positions 2 and 3 of the quinolone ring represents an optional bond; R is hydrogen or lower alkyl; R₁ is lower alkyl; and R₂, R₃ and R₄, which may be the same or different, are hydrogen, halo, lower alkyl, lower alkoxy, lower alkylthio, lower alkylsulphinyl, lower alkylsulphonyl, trifluoromethyl, cyano, fluorinated lower alkoxy, phenyl optionally substituted by one or two substituents selected from lower alkyl, lower alkoxy, lower alkylthio, halo and trifluoromethyl, the group —OAr or the group —S(O)$_n$Ar in which Ar is phenyl optionally substituted by one or two substituents selected from lower alkyl, lower alkoxy, lower alkylthio, halo and trifluoromethyl and n is 0, 1 or 2, or the group —NR₅R₆ or the N-oxide thereof in which R₅ and R₆, which may be the same or different, are lower alkyl or, together with the nitrogen atom to which they are attached, form a 5 to 7 membered ring optionally containing an additional hetero atom selected from oxygen, nitrogen and sulphur. The compounds reduce blood pressure when administered to hypertensive mammals.

Specific compounds disclosed in the Boots specification include:

7-Fluoro-1-methyl-4-oxo-1,4-dihydroquinoline-3carboxamide (Example 1b)

7-Chloro-1-methyl-4-oxo-1,4-dihydroquinoline-3carboxamide (Example 4)

7-Chloro-1,N-dimethyl-4-oxo-1,4-dihydroquino-line-3-carboxamide (Example 7).

SUMMARY OF THE INVENTION

In a product aspect the invention relates to compounds of the formula

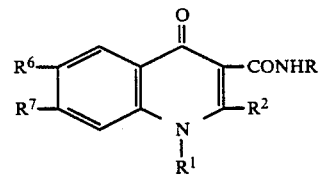

wherein R is hydrogen, hydroxy, amino, lower-alkyl or CH₂N═Z, wherein N═Z is di-lower-alkylamino, 1-pyrrolidyl, 1-piperidinyl or 4-morpholinyl; R¹ is lower-alkyl, lower-alkenyl, cycloalkyl, pyridinyl, or phenyl or phenylmethyl where phenyl can be substituted by from one to three substituents selected from halo, lower-alkyl, lower-alkoxy and trifluoromethyl;

R² is hydrogen, amino or hydroxy;

R⁶ is hydrogen or fluoro; and

R⁷ is pyridinyl, pyridinyl substituted by one or two lower-alkyl groups, pyridinyl-N-oxide, phenyl, 5-isoxazolyl, 3-methyl-5-isoxazolyl or 3-methyl-5-thiazolyl, with the proviso that when R is hydrogen or lower-alkyl, R¹ is lower-alkyl and R⁷ is phenyl, R² is other than hydrogen; and to pharmaceutically acceptable acid-addition salts thereof.

In a further product aspect the invention relates to compositions for combating herpes viruses which comprise an antivirally effective amount of a compound of Formula I in admixture with a suitable carrier or diluent.

In a process aspect, the invention relates to a method of combating herpes viruses which comprises contacting the locus of said viruses, including administration to a mammalian host, with a composition containing an antivirally effective amount of a compound of Formula I.

In a further process aspect the invention relates to methods for chemical synthesis of the compounds of Formula I comprising (a) reacting a compound of the formula

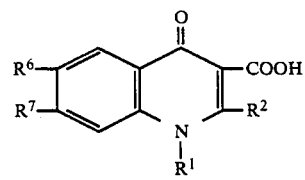

with carbonyldiimidazole and treating the resulting acylimidazole with ammonia or an amine, RNH₂; or (b) reacting a compound of the formula

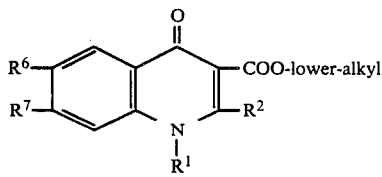

with ammonia or an amine, $RNH_2$; or (c) reacting a compound of the formula

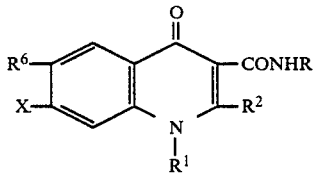

wherein X is chlorine, bromine or iodine with a compound of the formula $R^7Sn(Alk)_3$ where Alk is alkyl of 1–6 carbon atoms, in the presence of a palladium complex catalyst In still further product aspects, the invention relates to novel intermediates having the formulas

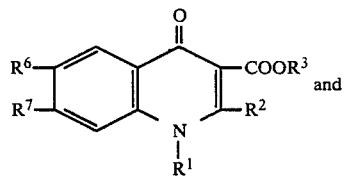

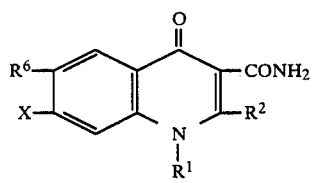

wherein $R^1$ is phenyl or phenylmethyl where phenyl can be substituted by one or two substituents selected from halo, lower-alkyl, lower-alkoxy and trifluoromethyl; $R^2$ is hydrogen or hydroxy; $R^3$ is hydrogen or lower-alkyl; $R^6$ is hydrogen or fluoro; $R^7$ is pyridinyl, pyridinyl substituted by one or two lower-alkyl groups, phenyl, 5-isoxazolyl, 3-methyl-5-isoxazolyl or 3-methyl-5-thiazolyl; and X is chloro, bromo or iodo.

DETAILED DESCRIPTION INCLUSIVE OF PREFERRED EMBODIMENTS

Throughout this specification the terms "loweralkyl" and "lower-alkoxy" stand for such groups having from one to six carbon atoms which may be straight or branched In the definition of $R^1$ in Formula I, the term "cycloalkyl" stands for such groups having three to six ring members; and the term "halo" stands for any of the four common halogen substituents, fluoro, chloro, bromo and iodo.

The invention also contemplates pharmaceutically acceptable acid-addition salts of the compounds of Formula I. The nature of the acid-addition salt is immaterial provided it is derived from an acid the anion of which is essentially innocuous to animal organisms. Examples of appropriate acid-addition salts include the hydrochloride, hydrobromide, sulfate, methanesulfonate, maleate, citrate, tartrate, p-toluenesulfonate, cyclohexanesulfamate, and the like.

In the preparation of compounds of Formula I from compounds of Formula II, the quinolinecarboxylic acid is caused to react with at least an equimolar amount of carbonyldiimidazole:

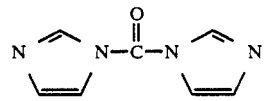

by heating the reactants in an inert solvent at a temperature between about 75° and 150° C. until the reaction is complete. The resulting acylimidazole:

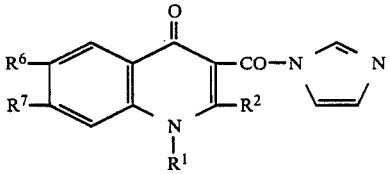

is then treated with ammonia or an amine, NHR, to give an amide of Formula I. The latter reaction takes place at room temperature in an inert solvent.

In the preparation of compounds of Formula I from compounds of Formula III, the quinolinecarboxylic acid ester is caused to react with a molar excess of ammonia or an amine, $NH_2R$ at a temperature between about 110° and 150° C. When ammonia or a volatile amine is used the reaction is carried out in an inert solvent, e.g. ethanol, in a sealed pressure vessel.

Alternatively, the compounds of Formula I where R is $CH_2N=Z$ can be prepared from the compounds of Formula I where R is hydrogen by reacting the latter with formaldehyde and the appropriate amine, $HN=Z$; or with the corresponding methylene quaternary, $CH_2=N+=Z$.

The compounds of Formula I where $R^7$ is pyridinyl-N-oxide are most conveniently prepared by oxidation of the corresponding pyridinyl compound with a peracid.

In the preparation of compounds of Formula I from compounds of Formula IV, the 7-haloquinolinecarboxamide is caused to react with an approximately equimolar amount of the organotin compound, $R^7Sn(Alk)_3$, in an inert solvent at a temperature between about 50° and 150° C., conveniently at the reflux temperature of the solvent The reaction is complete in a period ranging from 1–24 hours. Alternatively, the reactants and catalyst can be heated in a pressurized vessel in an inert atmosphere (e.g. argon, nitrogen) at a temperature between about 125° and 175° C. until the reaction is complete (1–5 hours). The palladium complex catalyst, present to the extent of about 5 mole percent, can be any such catalyst known to effect cross-coupling of organotin compounds with organic halides [cf. Kosugi et al., Bull. Chem. Soc. Japan 59, 677–679 (1986)], for example, $PdC1_2(PPh_3)_2$, $Pd(PPh_3)_4$, $PdCl_2[P(o-tolyl)_3]_2$, $PdCl_2+2P(OEt)_3$ and $PdCl_2(PhCN)_2$. A preferred catalyst is dichlorobis(triphenylphosphine)palladium $[PdCl_2(PPh_3)_2]$.

The intermediates of Formulas II, III and IV where $R^2$ is hydrogen are prepared by conventional procedures illustrated by the following Flow Sheet A:

FLOW SHEET A

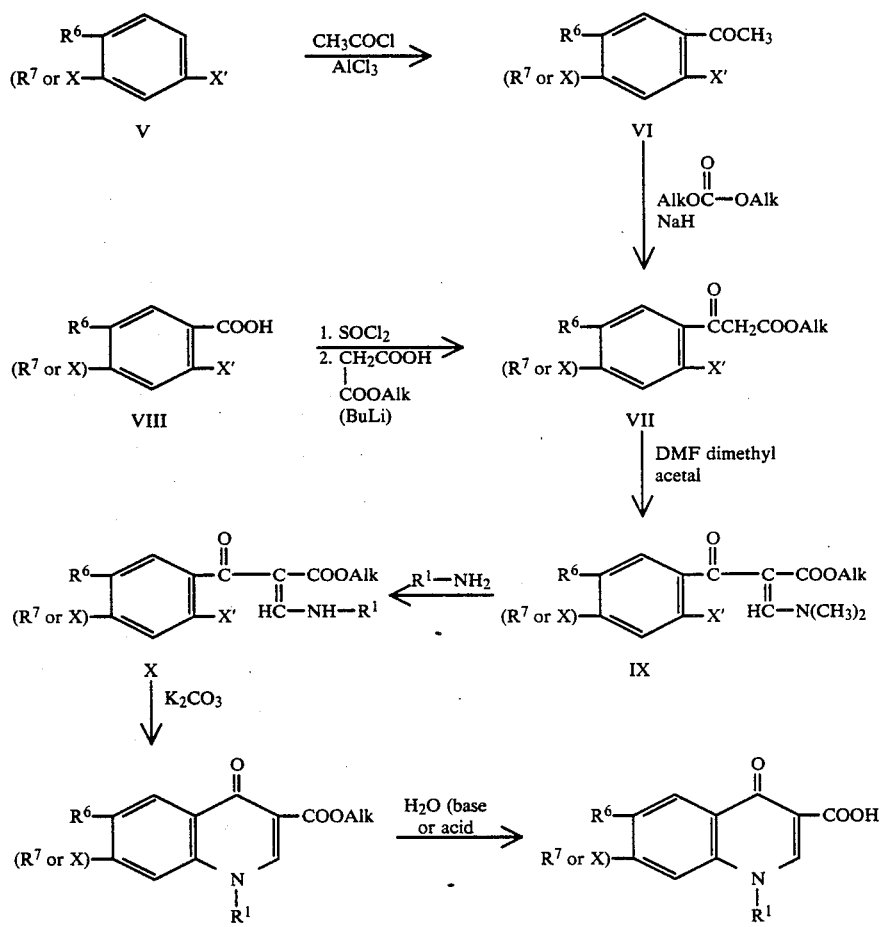

A halobenzene derivative (V; X'=F, Cl, Br or I) is subjected to a Friedel-Crafts reaction with acetyl chloride in the presence of aluminum chloride to give the corresponding halo substituted acetophenone (VI). The latter is caused to react with a dialkyl carbonate (Alk-=alkyl of 1-6 carbon atoms) in the presence of sodium hydride to give an alkyl benzoylacetate of Formula VII. The compound of Formula VII can alternatively be prepared from a halobenzoic acid (VIII) by first converting the latter to its acid chloride with thionyl chloride and treating the acid chloride with a half ester of malonic acid in the presence of butyllithium. The benzoylacetate (VII) is then treated with dimethylformamide (DMF) dimethyl acetal [(CH$_3$)$_2$NCH(OCH$_3$)$_2$] to form a 3-dimethylaminopropenoate (IX). The latter is then treated with an amine R$^1$NH$_2$ to produce the corresponding 3-R$^1$-aminopropenoate (X). Cyclization of X is carried out by heating in the presence of a base, preferably potassium carbonate, to give a quinolinecarboxylic acid ester corresponding to Formula III where R$^7$ is at C$_7$ and R$_2$ is H. The latter can be hydrolyzed to afford a quinolinecarboxylic acid corresponding to Formula II where R$^7$ is at C$_7$ and R$_2$ is H. The resulting esters and acids where X (halogen) is at C$_7$ may in turn be converted to amides of Formula IV by the procedures heretofore described.

Compounds of Formula I where R$^2$ is hydroxy can be prepared according to the following Flow Sheet B:

FLOW SHEET B

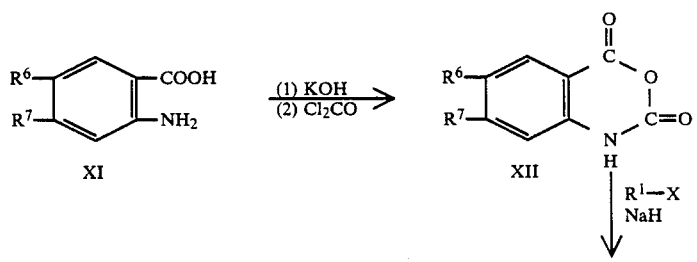

FLOW SHEET B

-continued

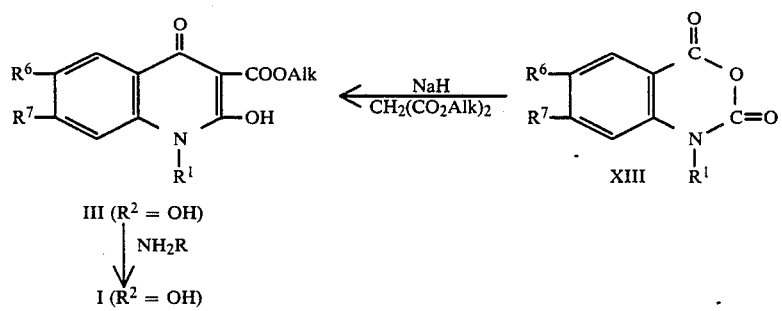

III ($R^2$ = OH)

↓ $NH_2R$

I ($R^2$ = OH)

A substituted 2amonibenzoic acid (XI) is converted to its potassium salt and caused to react with phosgene to yield a benzoxazine derivative of Formula XII. The latter is then alkylated with $R^2X$ (X=halogen) in the presence of sodium hydride to give XIII, which is then converted to a compound of Formula III ($R^2$=OH) by reaction with a malonic acid ester in the presence of sodium hydride. The ester (III) can be converted to the corresponding amide (I, $R^2$=OH) by the methods heretofore described.

Compounds of Formula I where $R^2$ is amino can be prepared according to the following Flow Sheet C:

FLOW SHEET C

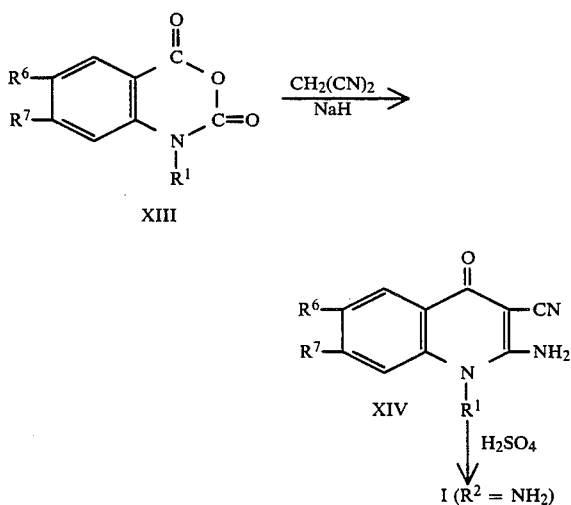

A compound of Formula XIII (see Flow Sheet B) is caused to react with malononitrile in the presence of sodium amide to afford a 3-quinolinecarbonitrile derivative of Formula XIV. The latter is then hydrolyzed with sulfuric acid to produce an amide of Formula I where $R_2$ is amino. An alternative synthetic approach to the compounds of Formula I where $R_2$ is amino is illustrated by Example 41 below.

The structures of the compounds were established by the modes of synthesis, by elementary analyses and by infrared, nuclear magnetic resonance and/or mass spectra.

The following examples will further illustrate the invention.

EXAMPLE 1

(a) 4-(3-Fluoro-4-methylphenyl)-1-trimethylacetyl-1,4-dihydropyridine

To a solution of 45 ml pyridine in 800 ml tetrahydrofuran (THF) was added dropwise 50 ml trimethylacetyl chloride. The mixture was stirred 3 hrs. at room temperature, 4.0 g cuprous iodide was added, and the mixture stirred for 1 hr. longer. The mixture was then cooled to $-40°$ C. and a Grignard reagent prepared from 45 ml 2-fluoro-4-chlorotoluene and 10 g magnesium in 300 ml THF was added dropwise The reaction mixture was stirred overnight at room temperature, ammonium chloride solution added, and the product was extracted and isolated to give 90 g of an oil used directly in the next reaction.

(b) 2-Fluoro-4-(4-pyridinyl)benzoic acid [VIII; X'=F., $R^6$=H, $R^7$=4-pyridinyl]

The product of part (a) (75.0 g) in 2 L water was heated on a steam bath, and 200 g potassium permanganate was added portion-wise. The reaction mixture was heated at 100° C. for three days and then filtered to remove manganese oxide. The filtrate was concentrated in vacuo and the residue dried to give 36.1 g of 2-fluoro-4-(4pyridinyl)benzoic acid.

(c) Ethyl 2-fluoro-4-(4-pyridinyl)benzoylacetate [VII; Alk =$C_2H_5$, X'=F, $R^6$=H, $R^7$=4-pyridinyl].

2-Fluoro-4-(4-pyridinyl)benzoic acid (6.6 g) was converted to its acid chloride by refluxing with 100 ml thionyl chloride and removal of excess thionyl chloride by distillation with acetonitrile.

To a solution of 12.0 g monoethyl malonate in 150 ml freshly distilled THF was added portionwise 75 ml n-butyllithium (2.5N in THF) at $-78°$ C. After half of the reagent had been added the mixture was warmed to $-10°$ C., the remainder of the reagent added and the mixture stirred for 20 min. The reaction mixture was cooled to $-60°$ C., the acid chloride prepared as described above was added, and the reaction mixture stirred for 30 min. at $-50°$ C., then allowed to warm to 0° C. and poured into 300 ml ether and 100 ml 1N hydrochloric acid. The mixture was neutralized and the ether layer dried and concentrated to give 5.3 g ethyl 2-fluoro-4-(4-pyridinyl)benzoylacetate as an oil used without further purification in the next reaction.

(d) Ethyl 3-dimethylamino-2-2-fluoro-4-(4-pyridinyl)benzoyl] propenoate [IX; Alk=$C_2H_5$, X'F, $R^6$=H, $R^7$=4-pyridinyl] 4-pyridinyl].

A mixture of 4.0 g ethyl 2-fluoro-4-(4-pyridinyl)benzoylacetate, 30 ml dimethylformamide dimethylacetal and 50 ml THF was stirred overnight at room temperature. The solvent was removed in vacuo to yield 3.5 g of product used directly in the next reaction.

(e) Ethyl 3-(4-fluorophenylamino)-2-2-fluoro-4-(4-pyridinyl)benzoyl]propenoate [X; Alk=C$_2$H$_5$, R$^1$=4-FC$_6$H$_4$, R$^6$=H, R$^7$=4-pyridinyl].

A mixture of 3.4 g of the product of part (d), 1.1 g 4-fluoroaniline and 20 ml THF was stirred overnight at room temperature. Dioxane was added and the THF distilled off. The resulting solution was heated at reflux overnight. The solvent was removed in vacuo. The residue was used directly in the next reaction (f) Ethyl 1-(4-fluorophenyl)-1,4-dihydro-4-oxo-7-(4-pyridinyl)3-quinolinecarboxylate [III; lower-alkyl C$_2$H$_5$,R$^1$=R$^1$=4-FC$_6$H$_4$, R$^2$=H, R$^6$=H, R$^7$=4-pyridinyl]

The residual product from part (e) and 1.4 g potassium carbonate (milled) in 25 ml dimethylformamide (DMF) was heated at reflux for 15 min. The solid product was isolated to obtain 3.5 g ethyl 1-(4-fluorophenyl)-1,4-dihydro-4-oxo-7-(4-pyridinyl)-3-quinolinecarboxylate, grayish-yellow solid, m.p. 252-253° C. when recrystallized from ethyl acetate.

(g) 1-(4-Fluorophenyl)-1,4-dihydro-4-oxo-7-(4-pyridinyl)3-quinolinecarboxylic acid [II; R$^1$=4—FC$_6$H$_4$, R$^2$=H, R$^6$=H, R$^7$=4-pyridinyl]

A mixture of 2.8 g of ethyl 1-(4-fluorophenyl)$_{1,4}$-dihydro-4-oxo-7-(4-pyridinyl)-3-quinolinecarboxylate, 20 ml of 10% potassium hydroxide solution and 10 ml ethanol was heated on a steam bath for 3 hrs. The reaction mixture was cooled and acidified with acetic acid. The solid product was collected and washed with acetone to give 2.6 g 1-(4-fluorophenyl)-1,4-dihydro-4-oxo-7-(4-pyridinyl)-3-quinolinecarboxylic acid. A sample of the compound was converted to its monomethanesulfonate salt, m.p. 280-281° C. when recrystallized from acetonitrile.

(h) 1-(4-Fluorophenyl)-1,4-dihydro-4-oxo-7-(4-pyridinyl)3-quinolinecarboxamide [I; R=H, R$^1$=4—FC$_6$H$_4$, R$^2$ =H, R$^6$ =H, R$^7$ =4-pyridinyl]

A mixture of 1.65 g 1-(4-fluorophenyl)-1,4-di-hydro4-oxo-7-(4-pyridinyl)-3-quinolinecarboxylic acid, 2.2 g of 1,1'-carbonyldiimidazole and 15 ml dimethylformamide (DMF) was heated at 150° C. for 1.5 hrs. The reaction mixture was poured into 50 ml concentrated ammonium hydroxide. The product was extracted with methylene dichloride and recovered therefrom to give 2.2 g 1-(4-fluorophenyl-1,4-dihydro-4-oxo-7-(4-pyridinyl)-3-quinolinecarboxamide which was converted to its monomethanesulfonate salt hemihydrate, m.p. 301°-303° C. (decompn.). The free base, prepared from the salt with potassium carbonate solution, had m.p. 315°-317° C. when recrystallized from DMF.

EXAMPLE 2

1-(4-Fluorophenyl)-1,4-dihydro-4-oxo-7-(N-oxide-4-pyridinyl)-3-quinolinecarboxamide

[I; R H, R$^1$ 4-FC6H4, R$^2$ =H, R$^6$ =H, R$^7$ =4-pyridinyl-N-oxide]

A mixture of 1.59 g 1-(4-fluorophenyl)-1,4-dihydro--4-oxo-7-(4-pyridinyl)-3-quinolinecarboxamide (Example 1h) and 1.53 g m-chloroperbenzoic acid in 50 ml of glacial acetic acid was stirred for 30 min. at room temperature. Additional m-chloroperbenzoic acid (0.38 g) was then added and stirring continued overnight. The product was isolated and recrystallized from methanol to give 1.14 g 1-(4-fluorophenyl)-1,4-dihydro-4-oxo-7-(N- oxide-4-pyridinyl)-3-quinolinecarboxamide in the form of a hemihydrate, m.p. above 300° C.

3

N-(Diethylaminomethyl)-1-(4-fluorophenyl)-1,4-dihydro-4-oxo-7-(4-pyridinyl)-3-quinolinecarboxamide

[I;·R CH$_2$N(C$_2$H$_5$)$_2$, R$^1$=4—FC$_6$H$_4$, R$^2$=H, R$^6$ =H, R$^7$ =4-pyridinyl].

A mixture of 2.2 g 1-(4-fluorophenyl)-1,4-di -hydro-4-oxo-7-(4-pyridinyl)-3-quinolinecarboxamide (Example 1h) and molar excess amounts of formaldehyde and diethylamine in 100 ml ethanol was heated at reflux for two days. The ethanol was removed and the residual product chromatographed on silica gel. The column was eluted with 10% isopropyl alcohol in chloroform; starting material was eluted first followed by fractions containing the desired N-diethylaminomethyl compound. The latter was recrystallized from ethyl acetate to give 0.9 g N-(diethylaminomethyl)-1-(4-fluorophenyl)-1,4-dihydro-4-oxo-7-(4-pyridinyl)-3-quinolinecarboxamide, m.p. 193195° C.

EXAMPLE 4

N-(4-Morpholinylmethyl)-1-(4-fluorophenyl)-1,4-dihydro-4-oxo-7-(4-pyridinyl)-3-quinolinecarboxamide

[I; R CH$_2$(4-morpholinyl), R$^1$4—FC$_6$H$_4$, R$^2$H, R$^6$ H, R$^7$4-pyridinyl]

A mixture of 1.08 g 1-(4-fluorophenyl)-1,4-di -hydro-4-oxo-7-(4-pyridinyl)-3-quinolinecarboxamide (Example 1 h), 0.45 g N-methylenemorpholinium chloride and 10 ml DMF was heated at 100° C. for 15 min. The reaction mixture was cooled, poured into 100 ml water and the pH adjusted to 8 with saturated sodium bicarbonate solution. The solid precipitate was collected, dried and recrystallized from an acetonitrile -chloroform mixture to give 0.90 g N-(4-morpholinylmethyl)-1-(4-fluorophenyl)$_{1,4}$-dihydro-4-oxo-7-(4-pyridinyl)-3-quinolinecarboxamide, m.p. 258-260° C.

EXAMPLE 5

N-(1-Piperidinylmethyl)-1-(4-fluorophenyl)-1,4-dihydro-4-oxo-7-(4-pyridinyl)-3-quinolinecarboxamide

[I; R CH$_2$(1-piperidinyl), R$^1$4—FC$_6$H$_4$, R$^2$H, R$^6$H, R$^7$=4-pyridinyl]was prepared by the procedure of Example 4 by substituting the N-methylenemorpholinium chloride with an equivalent amount of N-methylenepiperidinium chloride, and was obtained (0.85 g) in the form of a colorless solid, m.p. 241-243° C. (from ethyl acetate).

Similarly, N-(1-pyrrolidinylmethyl)-1-(4-fluorophenyl)-1,4-dihydro-4-oxo-7-(4-pyridinyl)-1-quinolinecarboxamide can be prepared using N-methylenepyrrolidinium chloride.

EXAMPLE 6

1-Ethyl-1,4-dihydro-4-oxo-7-(4-pyridinyl)-3-quinolinecarboxamide

[I; R=H, R$^1$32 C$_2$H$_5$, R$^2$=H, R$^6$=H, R$^7$=4-pyridinyl]

To a stirred solution of 12.16 g 1,1,-carbonyldiimidazole in 150 ml DMF was added 14.72 g 1-ethyl-1,4- dihydro-4-oxo-7-(4-pyridinyl)-3-quinolinecarboxylic acid (U.S. Pat. No. 3,753,993). The mixture was heated at 100° C. for 2 hrs. and allowed to cool overnight. The solid product was collected and washed with ethyl acetate to give 15.22 g colorless crystals, m.p. 281-287° C. The latter material, which is the acylimidazole derivative, was suspended in 200 ml DMF and anhydrous ammonia was bubbled through the solution for 1 hr. The reaction mixture was filtered and the solid product washed with ethyl acetate and ether to give 12.85 g of colorless powder which was recrystallized from hot DMF to give 11.6 g 1-ethyl-1,4-dihydro-4-oxo-7-(4-pyridinyl)-3-quinolinecarboxamide, m.p. 314–317° C.

The hydrochloride salt form was obtained as a pale-yellow solid, m.p. above 300° C.

The monomethanesulfonate salt was obtained in the form of a colorless solid, m.p. 301–303° C.

EXAMPLE 7

1-Ethyl-1,4-dihydro-4-oxo-7-(2,6-dimethyl-4-pyridinyl)-3quinolinecarboxamide

[I; $R=H$, $R^1=C_2H_5$, $R^2=H$, $R^6=H$, $R^7=2,6$-dimethyl-4-pyridinyl] was prepared from 10 g 1-ethyl-1,4-dihydro-4-oxo-7-(2,6-dimethyl-4-pyridinyl)-3quinolinecarboxylic acid (U.S. Pat. No. 3,753,993) according to the procedure of Example 6 without isolation of the intermediate acylimidazole, and was obtained (7.1 g) as a colorless solid, m.p. 289°–290° C. when recrystallized from DMF-ether.

EXAMPLE 8

1,4-Dihydro-1-(4-methoxyphenyl)-4-oxo-7-(4-pyridinyl)-3quinolinecarboxamide

[I; $R=H$, $R^1=4\text{-}CH_3OC_6H_4$, $R^2=H$, $R^6=H$, $R^7=4$-pyridinyl] was prepared from 3.0 g 1,4-di-hydro-1-(4-methoxyphenyl)-4-oxo-7-(4-pyridinyl)-3-quinolinecarboxylic acid by the procedure of Example 1, part (h), and was obtained (2.8 g) in the form of its methanesulfonate salt hemihydrate, pale-yellow powder, m.p. 281°–282° C. when recrystallized from methanol.

The starting material was obtained by hydrolysis of the corresponding ethyl ester, in turn prepared according to the procedures of Example 1, parts (e) and (f), substituting 4-methoxyaniline for the 4-fluoroaniline in part (e).

EXAMPLE 9

1-[4-(1,1-Dimethylethyl)phenyl]-1,4-dihydro-4-oxo-7-(4-pyridinyl)-3-quinolinecarboxamide

[I; R H, $R^1 4\text{-}(CH_3)_3CC_6H_4$, $R^2H$, $R^6H$, $R^7$ 4-pyridinyl] was prepared from 5.0 g 1-[4-(1,1-dimethylethyl)-phenyl]-1,4-dihydro-4-oxo-7-(4-pyridinyl)-3-quinolinecarboxylic acid by the procedure of Example 1, part (h), and was obtained (2.4 g) in the form of its methanesulfonate salt hemihydrate, m.p. 225°–228° C. when recrystallized from methanol.

The starting material, 1-[4-(1,1-dimethylethyl)-phenyl]-1,4-dihydro-4-oxo-7-(4-pyridinyl)-3-quinolinecarboxylic acid (monomethanesulfonate hemihydrate, m.p. 251°–252° C. from methanol) was prepared according to the procedures of Example 1, parts (e), (f) and (g), substituting 4-(t-butyl)aniline for the 4-fluoroaniline in part (e).

EXAMPLE 10

1,4-Dihydro-4-oxo-1,7-di(4-pyridinyl)-3-quinolinecarboxamide

[I; $R=H$, $R^1=4$-pyridinyl, $R^2=H$, $R^6=H$, $R^7=4$-pyridinyl] was prepared from 2.6 g 1,4-dihydro-4-oxo1,7-di(4-pyridinyl)-3-quinolinecarboxylic acid by the procedure of Example 1, part (h), and was obtained (2.6 g) in the form of its dimethanesulfonate salt monohydrate, light-tan powder, m.p. above 300° C. when recrystallized from 95% ethanol.

The starting acid was obtained according to the procedures of Example 1, parts (e), (f) and (g), substituting 4-aminopyridine for the 4-fluoroaniline of part (e).

EXAMPLE 11

1-Cyclopropyl-1,4-dihydro-4-oxo-7-(4-pyridinyl)-3-quinolinecarboxamide

[I; $R=H$, $R^1=$cyclopropyl, $R^2=H$, $R^6=H$, $R^7=4$-pyridinyl] was prepared from 2.1 g 1-cyclopropyl-1,4-dihydro-4-oxo-7-(4-pyridinyl)-3-quinolinecarboxylic acid by the procedure of Example 1, part (h), and was obtained (1.8 g) in the form of its methanesulfonate salt, m.p. 310° C. (decompn.) when recrystallized from methanol.

The starting acid, 1-cyclopropyl-1,4-dihydro-4-oxo-7-(4-pyridinyl)-3-quinolinecarboxylic acid (methanesulfonate ·¼ $H_2O$, light-yellow powder, m.p. 278°–281° C.) was prepared by hydrolysis of the corresponding ethyl ester (m.p. 208°–211° C.), which was in turn obtained according to the procedures of Example 1, parts (e) and (f), substituting cyclopropylamine for the 4-fluoroaniline of part (e).

EXAMPLE 12

1-(3,4-Dichlorobenzyl)-1,4-dihydro-4-oxo-7-(4-pyridinyl)-3-quinolinecarboxamide

[I; $R=H$, $R^1 3,4\text{-}Cl_2C_6H_3CH_2$, $R^2=H$, $R^6=H$, $R^7=4$-pyridinyl] was prepared from 2.82 g 1-(3,4-dichlorobenzyl)-1,4-dihydro-4-oxo-7-(4-pyridin-yl)-3-quinolinecarboxylic acid according to the procedure of Example 6 but without isolation of the intermediate acyimidazole, and was obtained (1.0 g) in the form of its methanesulfonate salt, yellowish-tan powder, m.p. 260°–276° C. when recrystallized from methanol.

The starting acid was obtained according to the procedures of Example 1, parts (e), (f) and (g), substituting 3,4-dichlorobenzylamine for the 4-fluoroaniline of part (e).

EXAMPLE 13

1,4-Dihydro-1-(3,4-dimethylphenyl)-4-oxo-7-(4-pyridinyl)-3-quinolinecarboxamide

[I; R H, $R^1 3,4\text{-}(CH_3)_2C_6H_3$, $R^2=H$, $R^6=H$, $R^7=4$-pyridinyl] was prepared from 3.08 g 1,4-dihydro-1-(3,4-dimethylphenyl)-4-oxo-7-(4-pyridin-yl-3-quinolinecarboxylic acid according to the procedure of Example 6 but without isolation of the intermediate acylimidazole, and was obtained (2.1 g) in the form of its methanesulfonate salt monohydrate, yellowish-tan powder, m.p. 244°–264° C. (decompn.) when recrystallized from methanol.

The starting acid, 1,4-dihydro-1-(3,4-dimethylphenyl)-4-oxo-7-(4-pyridinyl)-3-quinolinecarboxylic acid (hydrochloride salt, tan powder, m.p. 301°–303° C.) was prepared by hydrolysis of the corresponding ethyl ester (m.p. 208°–210° C. from ethyl acetate/hexane), which in turn was obtained according to the procedures of Example 1, parts (e) and (f), substituting 3,4-dimethylaniline for the 4-fluoroaniline of part (e).

EXAMPLE 14

1-(3,4-Dichlorophenyl)-1,4-dihydro-4-oxo-7-(4-pyridinyl)-3-quinolinecarboxamide

[I; $R=H$, $R^1=3,4-Cl_2C_6H_3$, $R^2=H$, $R^6=H$, $R^7=4$-pyridinyl] was prepared from 4.73 g 1-(3,4-dichlorophenyl)-1,4-dihydro-4-oxo-7-(4-pyridinyl)-3-quinolinecarboxylic acid according to the procedure of Example 6 but without isolation of the intermediate acylimidazole, and was obtained (2.25 g) in the form of its methansulfonate salt monohydrate, tan solid, m.p. 282° C. (decompn.) when recrystallized from methanol The starting acid was prepared by hydrolysis of ethyl 1-(3,4-dichlorophenyl)-1,4-dihydro-4-oxo-7-(4-pyridinyl)-3-quinolinecarboxylate (tan solid, m.p. 238°–240° C. when recrystallized from toluene), in turn prepared according to the procedures of Example 1, parts (e) and (f), substituting 3,4-dichloroaniline for the 4-fluoroaniline of part (e).

EXAMPLE 15

1-(2,4-Difluorophenyl)-1,4-dihydro-4-oxo-7-(4-pyridinyl)-3-quinolinecarboxamide

[I; R H, $R^1=2,4-FC_6H_3$, $R^2$ H, $R^6=H$, $R^7=4$-pyridinyl] was prepared from 3.33 g 1-(2,4-difluorophenyl)-1,4-dihydro-4-oxo-7-(4-pyridinyl)3-quinolinecarboxylic acid according to the procedure of Example 1, part (h), and was obtained (1.85 g) in the form of its methanesulfonate salt monohydrate, yellowish-tan powder, m.p. 302°–303° C. when recrystallized from methanol.

The starting acid, 1-(2,4-difluorophenyl)-1,4-dihydro-4-oxo-7-(4-pyridinyl)-3-quinolinecarboxylic acid (tan solid, m.p. 291°–292° C. (decompn.)) was prepared by hydrolysis of the corresponding ethyl ester (pale-yellow powder, m.p. 216°–218° C. from ethanol), in turn obtained according to the procedures of Example 1, parts (e) and (f), substituting 2,4-difluoroaniline for the 4-fluoroaniline of part (e).

EXAMPLE 16

1,4-Dihydro-1-methyl-4-oxo-7-(4-pyridinyl)-3-quinolinecarboxamide

[I; R=H, $R^1=CH_3$, $R^2=H$, $R^6=H$, $R^7=4$-pyridinyl] was prepared from 4.45 g 1,4-dihydro-1-methyl-4-oxo-7-(4-pyridinyl)-3-quinolinecarboxylic acid (U.S. Pat. No. 3,753,993) according to the procedure of Example 6, and was obtained (3.54 g) in the form of its hydrochloride salt, colorless solid, m.p. above 300° C., crystallized from ethanol.

EXAMPLE 17

1-Butyl-1,4-dihydro-4-oxo-7-(4-pyridinyl)-3-quinolinecarboxamide

[I; R=H, $R^1=(CH_2)_3CH_3$, $R^2=H$, $R^6=H$, $R^7=4$-pyridinyl] was prepared from 5.85 g 1-butyl-1,4-dihydro-4-oxo-7-(4-pyridinyl)-3-quinolinecarboxylic acid according to the procedure of Example 6, but without isolation of the intermediate acylimidazole, and was obtained (4.0 g) in the form of its methanesulfonate salt, pale-yellow solid, m.p. 267°–269° C. from methanol.

The starting acid was prepared by hydrolysis of the corresponding ethyl ester which in turn was prepared by alkylation of ethyl 1,4-dihydro-4-oxo-7-(4-pyridinyl)-3-quinolinecarboxylate with 1-iodobutane (cf. U.S. Pat. No. 3,753,993).

EXAMPLE 18

1,4-Dihydro-4-oxo-1-propyl-7-(4-pyridinyl)-3-quinolinecarboxamide

[I; R=H, $R^1=(CH_2)_2CH_3$, $R^2=H$, $R^6=H$, $R^7=4$-pyridinyl] was prepared from 3.24 g 1,4-dihydro-4-oxo-1-propyl-7-(4-pyridinyl)-3-quinolinecarboxylic acid (U.S. Pat. No. 3,753,993) according to the procedure of Example 6, but without isolation of the intermediate acylimidazole, and was obtained (1.72 g) in the form of its methanesulfonate salt, yellow powder, m.p. 303–305° C. (from methanol).

EXAMPLE 19

1,4-Dihydro-4-oxo-1-(2-propenyl)-7-(4-pyridinyl)-3-quinolinecarboxamide

[I; R=H, $R^1=CH_2CH=CH_2$, $R^2=H$, $R^6=H$, $R^7=4$-pyridinyl] was prepared from 3.5 g 1,4-dihydro-4-oxo-1-(2-propenyl)-7-(4-pyridinyl)-3-quinolinecarboxylic acid according to the procedure of Example 1, part (h), and was obtained (1.9 g) in the form of its methanesulfonate salt as a pale-yellow powder, m.p. above 300° C. (from ethanol/methanol).

The starting acid, 1,4-dihydro-4-oxo-1-(2-propenyl)-7-(4-pyridinyl)-3-quinolinecarboxylic acid (golden crystals, m.p. 259.5°–261° C. from methanol), was prepared by hydrolysis of the corresponding ethyl ester (yellow powder, m.p. 155°–157° C.), in turn prepared by alkylation of ethyl 1,4-dihydro-4-oxo-7-(4-pyridinyl)-3-quinolinecarboxylate with allyl bromide.

EXAMPLE 20

1-Ethyl-1,4-dihydro-4-oxo-7-(2-pyridinyl)-3-quinolinecarboxamide

[I; R=H, $R^1C_2H_5$, $R^2H$, $R^6H$, $R^7$-pyridinyl] was prepared from 2.94 g 1-ethyl-1,4-dihydro-4-oxo-7-(2-pyridinyl)-3-quinolinecarboxylic acid (U.S. Pat No. 3,753,993) according to the procedure of Example 1, part (h), and was obtained (2.66 g) in the form of a light-tan solid, m.p. 245°–246° C.

EXAMPLE 21

1,4-Dihydro-4-oxo-1-phenyl-7-(4-pyridinyl)-3-quinolinecarboxamide

[I; R=H, $R^1C_6H_5$, $R^2H$, $R^6H$, $R^7=4$-pyridinyl] was prepared from 2.4 g 1,4-dihydro-4-oxo-1-phenyl-7-(4-pyridinyl)-3-quinolinecarboxylic acid according to the procedure of Example 1, part (h), and was obtained (1.6 g) in the form of a tan powder, m.p. 301°–303° C. (decompn.) when recrystallized from acetonitrile.

The starting acid, 1,4-dihydro-4-oxo-1-phenyl7-(4-pyridinyl)-3-quinolinecarboxylic acid (tan powder, m.p. above 325° C., from acetonitrile) was prepared by hydrolysis of the corresponding ethyl ester (tan powder, m.p. 288°–289° C., from ethylene dichloride—ethyl acetate), in turn prepared according to the procedures of Example 1, parts (e) and (f), substituting aniline for the 4-fluoroaniline in part (e).

EXAMPLE 22

(a) Ethyl 7-bromo-1,4-dihydro-1-(4-fluorophenyl)-4-oxo-3quinolinecarboxylate.

A mixture of 31.3 g ethyl 3-(4-fluorophenyl-amino)-2-(4-bromo-2-chlorobenzoyl)propenoate and 15.3 g anhydrous milled potassium carbonate in 150 ml DMF was stirred for one hour at room temperature. The reaction mixture was filtered and the filtrate chilled to cause precipitation of the product (25.6 g), m.p. 268.5°–270° C.

The starting material was prepared by conventional procedures starting from the lithium salt of monoethyl malonate and 4-bromo-2-chlorobenzoyl chloride which reacted to form ethyl 4-bromo-2-chlorobenzoylacetate. The latter was caused to react with dimethylformamide dimethylacetal to give ethyl 3-dimethylamino-2-(4-bromo2-chlorobenzoyl)propenoate, which by reaction with 4-fluoroaniline afforded said starting material.

(b) Ethyl 1,4-dihydro-1-(4-fluorophenyl)-4-oxo-7-(trimethylsilylethynyl)-3-quinolinecarboxylate.

To a solution of 25.4 g ethyl 7-bromo-1,4-dihydro-1-(4-fluorophenyl)-4-oxo-3-quinolinecarboxylate in 975 ml acetonitrile at 40°–50° C. was added 1.4 g cuprous iodide and 325 ml triethylamine. The air in the reaction was replaced by argon, and 1.4 g bis-triphenylphosphine palladium dichloride and 15.5 ml trimethylsilylacetylene were added. The reaction mixture was heated at reflux for one hour, then chilled to 0° C, and the product was collected to give 23.4 g ethyl 1,4-dihydro-1-(4-fluoro-phenyl)-4-oxo-7-(trimethylsilylethynyl)-3-quinolinecarboxylate. A sample of the compound was further purified by recrystallization from DMF to give a colorless solid, m.p. 247°–249° C. The corresponding carboxylic acid, obtained by hydrolysis of the ester with ethanolic hydrogen chloride, was obtained as a light-tan powder, m.p. 289° C. (decompn.).

(c) Ethyl 1,4-dihydro-7-ethynyl-1-(4-fluorophenyl)-4-oxo3-quinolinecarboxylate.

A mixture of 23.3 g ethyl 1,4-dihydro-1-(4-fluorophenyl)-4-oxo-7-(trimethylsilylethynyl)-3-quinolinecarboxylate, 10.5 g potassium fluoride and 700 ml ethanol was heated at reflux for 4 hrs. The reaction mixture was concentrated in vacuo and the residue triturated with chloroform. The chloroform-soluble fraction was isolated and recrystallized from ethyl acetate to give 14.02 g ethyl 1,4-dihydro-7-ethynyl-1-(4-fluorophenyl)-4-oxo-3quinolinecarboxylate, m.p. 227°–229° C. d) 1,4-dihydro-1-(4-fluorophenyl)-7-(3-methyl-5

Ethyl isoxazolyl)-4-oxo-3-quinolinecarboxylate.

A solution of 9.8 g nitroethane and 13 ml triethylamine in 130 ml chloroform was added dropwise to a solution of 10.47 g ethyl 1,4-dihydro-7-ethynyl-1-(4-fluorophenyl)-4-oxo-3-quinolinecarboxylate and 15.5 g phenyl isocyanate in 80 ml chloroform over a period of concentrated in vacuo. The residue was crystallized in ether and recrystallized from acetonitrile to give 8.60 g ethyl 1,4-dihydro-1-(4-fluorophenyl)-7-(3-methyl-5-isoxazolyl)4-oxo-3-quinolinecarboxylate (yellow solid, m.p. 214°–216° C.).

(e) 1,4-Dihydro-1-(4-fluorophenyl)-7-(3-methyl-5-isoxazolyl)-4-oxo-3-quinolinecarboxylic acid, m.p. 281°–282° C. (from DMF) was prepared by hydrolysis of the ester of part (d) by heating in ethanolic potassium hydroxide.

(f) 1,4-Dihydro-1-(4-fluorophenyl)-7-(3-methyl-5-isoxazolyl-4-oxo-3-quinolinecarboxamide [I; R=H, $R^1$=4—$FC_6H_4$, $R^2$=H, $R^6$=H, $R^7$=3-methyl-5-isoxazolyl] was prepared from 4.71 g of the acid of part (e) according to the procedure of Example 1, part (h), and was obtained (3.92 g) as a colorless solid, m.p. above 300° C. when recrystallized from DMF.

EXAMPLE 23

(a) Ethyl 7-3-(dimethylamino)-1-oxo-2-butenyl-1-ethyl1,4-dihydro-4-oxo-3-quinolinecarboxylate.

A mixture of 32.6 g ethyl 7-acetyl-1,4-dihydro1-ethyl-4-oxo-3-quinolinecarboxylate, 24 ml dimethylacetamide dimethylacetal and 100 ml DMF was heated on a steam bath for 4 hrs. The reaction mixture was concentrated in vacuo and the solid residue triturated with ethyl acetate. The solid product was recrystallized from acetonitrile to give 20.9 g ethyl 7-[3-(dimethylamino)-1-oxo2-butenyl]-1-ethyl-1,4-dihydro-4-oxo-3-quinolinecarboxylate, yellowish-orange powder, m.p. 178–179.5° C.

The starting material was prepared by conventional methods from 3-acetylaniline. The latter was reacted with diethyl ethoxymethylenemalonate to form the EMME adduct which by heating in Dowtherm was cyclized to ethyl 7-acetyl-1,4-dihydro-4-oxo-3-quinolinecarboxylate. The latter was then alkylated with ethyl iodide in the presence of potassium carbonate to produce said starting material.

(b) Ethyl 1-ethyl-7-(3-methyl-5-isoxazolyl)-1,4-dihydro-4-oxo-3-quinolinecarboxylate.

A mixture of 14.4 g ethyl 7-[3-(dimethylamino)-1-oxo-2-butenyl]-1-ethyl-1,4-dihydro-4-oxo-3-quinolinecarboxylate, 3.20 g hydroxylamine hydrochloride and 90 ml ethanol was stirred at reflux for 15 hrs. The reaction mixture was cooled to 0° C. and the crystalline product which formed was collected, triturated with water and dried to give 12.3 g of product, m.p. 177°–180° C. The latter was recrystallized from acetonitrile to give ethyl 1-ethyl-7-(3-methyl-5-isoxazolyl)-1,4-dihydro-4-oxo-3quinolinecarboxylate, m.p. 180°–185° C.

(c) 1-Ethyl-1,4-dihydro-7-(3-methyl-5-isoxazolyl)-4-oxo-3quinolinecarboxylic acid, m.p. 269°–271° C., was prepared by hydrolysis of the ester of part (b) with aqueous hydrogen chloride. (d) 1-Ethyl-1,4-dihydro-7-(3-methyl-5-isoxazolyl)-4-oxo-3-quinolinecarboxamide [I; R =H, $R^1$=$C_2H_5$, $R_2$=H, $R_6$=H, $R_H$, $R^7$=3-methyl-5-isoxazolyl] was prepared from 2.98 g acid of part (c) according to the procedure of Example 1 part (h), and was obtained (2.80 g) as a colorless solid, m.p. above 300° C. when recrystallized from DMF.

EXAMPLE 24

(a) Ethyl 1-ethyl-1,4-dihydro-7-(5-isoxazolyl)-4-oxo-3-quinolinecarboxylate was prepared from 30.8 g ethyl 7-[3-(dimethylamino)-1-oxo-2-propenyl]-1-ethyl-1,4-dihydro-4oxo-3-quinolinecarboxylate and 6.95 g hydroxylamine hydrochloride according to the procedure of Example 23, part (b), and was obtained (28.1 g) in the form of a light-tan solid, m.p. 180–183° C. when recrystallized from ethanol.

The starting material was prepared according to the procedure of Example 23, part (a), substituting dimethylformamide dimethylacetal for the dimethylacetamide dimethylacetal of that example. (b) 1-Ethyl-1,4-dihydro-7-(5-isoxazolyl)-4-oxo-3-quinolinecarboxylic acid, m.p. 277–280° C., was prepared by hydrolysis of the ester of part (b) with aqueous hydrogen chloride. (c) 1-Ethyl-1,4-dihydro-7-(5-isoxazolyl)-4-oxo-3-quinolinecarboxamide [I; R =H, $R^1$=$C_2H_5$, $R^2$=H, R=H, R7 =5-isoxazolyl] was prepared from 16.0 g acid of part (b) according to the procedure of Example 1, part (h), and was obtained (11.8 g) in the form of a pale-yellow solid, m.p. 243–245° C. when recrystallized from DMF.

EXAMPLE 25

1-Ethyl-6-fluoro-1,4-dihydro-4-oxo-7-(4-pyridinyl)-3quinolinecarboxamide [I; R=H, $R^1$=$C_2H_5$, $R_2$=H, $R_6$=F, $R_7$=4-pyridinyl] was prepared from 201 mg 1-ethyl-6-fluoro-1,4-dihydro-4-oxo-7-(4-pyridinyl)-3-quinolinecarboxylic acid according to the procedure of Example 1, part (h) and was obtained (119 mg) in the form of a pale-orange powder, m.p. 321–323° C. when recrystallized from DMF.

The starting acid was prepared by hydrolysis of the corresponding ethyl ester, in turn prepared from the known 6-des-fluoro compound by nitration to form the 6-nitro compound, reduction to the 6-amino compound, and conversion of the latter to the 6-fluoro compound by the diazotization procedure of J. Org. Chem. 26, 5149 (1961).

EXAMPLE 26

1,4-Dihydro-4-oxo-1-pentyl-7-(4-pyridinyl)-3-quinolinecarboxamide [I; R=H, $R^1$=(CH$_2$)$_4$CH$_3$, $R_2$=H, $R_6$=H, $R_7$=4-pyridinyl] was prepared from 4.0 g 1,4-dihydro-4-oxo-1-pentyl-7-(4-pyridinyl)-3-quinolinecarboxylic acid according to the procedure of Example 6, but without isolation of the intermediate acylimidazole, and was obtained (3.29 g) in the form of a pale-yellow solid, m.p. 188–190° C. when recrystallized from ethyl acetate.

The starting acid was prepared by hydrolysis of the corresponding ethyl ester, which in turn was prepared by alkylation of the known ethyl 1,4-dihydro-7-(4-pyridinyl)-4-oxo-3-quinolinecarboxylate with pentyl halide.

EXAMPLE 27

(a)

1,4-Dihydro-1-ethyl-7-(3-pyridinyl)-4-oxo-3-quinolinecarboxylic acid.

A suspension of 10.0 g ethyl 7-bromo-1,4-dihydro-1-ethyl-4-oxo-3-quinolinecarboxylate (U.S. Pat. No. 3,753,993), 0.64 g dichlorobis(triphenylphosphine)palladium, 10.9 g 3-trimethylstannylpyridine and 6.5 ml hexamethylphosphoramide in 40 ml dioxane was heated at reflux under nitrogen for 48 hrs. The reaction mixture was filtered through neutral alumina, eluted with chloroform, washed with water, and dried over potassium carbonate. The solid product obtained by concentration in vacuo was subjected to chromatography (MPLC; 10:1 CHCl$_3$/EtOH) to give 5.6 g of ethyl 1,4-dihydro-1-ethyl-7-(3-pyridinyl)4-oxo-3-quinolinecarboxylate, which was hydrolyzed by refluxing with 150 ml 3N hydrochloric acid for 1.5 hrs. The product which separated (3.9 g) was dried to give 1,4-dihydro-1-ethyl-7-(3-pyridinyl)-4-oxo-3-quinolinecarboxylic acid, m.p. 268–269° C.

The 3-trimethylstannylpyridine reagent was prepared from 3-bromopyridine by reacting the latter with n-butyllithium under nitrogen at −78° C., followed by addition of one equivalent of trimethylstannyl chloride. Aqueous work-up and concentration in vacuo gave 3-trimethylstannylpyridine in 79% yield.

(b) 1-Ethyl-1,4-dihydro-4-oxo-7-(3-pyridinyl)-3-quinolinecarboxamide [I; R=H, R=C$_2$H$_5$, $R_2$=H, $R_6$=H, $R_7$=3-pyridinyl] was prepared from 3.9 g acid of part (a) according to the procedure of Example 1, part (h), and was obtained (2.8 g) in the form of a colorless solid, m.p. 275–277° C. when recrystallized from DMF.

Example 28

(b) 1-Ethyl-1,4-dihydro-N-methyl-4-oxo-7-(4-pyridinyl)-3quinolinecarboxamide [I; R=CH$_3$, $R^1$=C$_2$H$_5$, $R_2$=H, $R_6$=H, $R_7$=4-pyridinyl] was prepared from 14.72 g 1-ethyl1,4-dihydro-4-oxo-7-(4-pyridinyl)-3-quinolinecarboxylic acid according to the procedure of Example 6, except that instead of anhydrous ammonia, anhydrous methylamine was used to decompose the intermediate acylimidazole; there was obtained in 90% yield the desired amide in the form of colorless needles, m.p. 275–278° C. when recrystallized from DMF.

EXAMPLE 29

1-Ethyl-1,4-dihydro-4-oxo-7-(4-pyridinyl)-3-quinolinecarboxylic acid hydrazide [I; R=NH$_2$, $R^1$=C$_2$H$_5$, $R_2$=H, $R_6$=H, $R_7$=4-pyridinyl].

To a slurry of the intermediate acylimidazole of Example 6 (10.2 g) in 200 ml DMF was added 5.0 ml 95% hydrazine. The reaction mixture was stirred for 3 hrs., and the solid product was collected by filtration, washed with DMF and dried to give 6.7 g 1-ethyl-1,4-dihydro-4-oxo-7-(4-pyridinyl)-3-quinolinecarboxylic acid hydrazide, m.p. 274–275° C.

EXAMPLE 30

1-Ethyl-1,4-dihydro-N-hydroxy-4-oxo-7-(4-pyridinyl)-3quinolinecarboxamide [I; R OH, $R^1$=C$_2$H$_5$, $R_2$=H, $R_6$=H, $R_7$=4-pyridinyl].

To a slurry of the intermediate acylimidazole of Example 6 (15.0 g) in 200 ml pyridine was added 6.1 g hydroxylamine hydrochloride, and the mixture was stirred for 4 hrs. The pyridine was stripped in vacuo, and the residue was washed with water, dried, and crystallized from DMF-ether to give 10.2 g 1-ethyl-1,4-dihydro-N-hydroxy-4-oxo-7-(4-pyridinyl)-3-quinolinecarboxamide, m.p. 245° C. (decompn.).

EXAMPLE 31

1-(4-Bromophenyl)-1,4-dihydro-7-(4-pyridinyl)-4-oxo-3quinolinecarboxamide [I; R H, $R^1$ 4-BrC$_6$H$_4$, $R_2$=H, $R_6$=H, $R_7$=4-pyridinyl].

Anhydrous ammonia was bubbled through a suspension of 3.00 g ethyl 1-(4-bromophenyl)-1,4-dihydro-7-(4-pyridinyl)-4-oxo-3-quinolinecarboxylate in 200 ml ethanol in a stainless steel bomb for 30 min. The bomb was sealed and heated at 125° C. with stirring overnight. The bomb was cooled and the contents concentrated in vacuo. The residue was triturated with ether and the remaining solid crystallized from methanol containing 1 ml methanesulfonic acid. There separated 2.15 g 1-(4-bromophenyl)-1,4-dihydro-7-(4-pyridinyl)-4-oxo-3-quinolinecarboxamide in the form of its monomethanesulfonate monohydrate, tan solid, m.p. 294–297° C.

The starting ester was prepared according to the procedures of Example 1, substituting 4-bromoaniline for the 4-fluoroaniline in part (e) of that Example.

EXAMPLE 32

1-(4-Chlorophenyl)-1,4-dihydro-7-(4-pyridinyl)-4-oxo-3quinolinecarboxamide [I; R=H, $R^1$ 4-ClC$_6$H$_4$, $R_2$=H, $R_6$=H, $R_7$=4-pyridinyl] was prepared from 3.40 g ethyl 1-(4-chlorophenyl)-1,4-dihydro-7-(4-pyridinyl)-4-oxo-3quinolinecarboxylate and ammonia according to the procedure of Example 31, except that the ammonia was added at a temperature about −70° C. (Dry ice-/acetone bath). There was obtained 2.06 g of the desired amide in the form of its methanesulfonate monohydrate, yellowish-tan solid, m.p. 280° C.

The starting ester, tan solid, m.p. 231–233° C., was prepared according to the procedures of Example 1, substituting 4-chloroaniline for the 4-fluoroaniline in part (e) of that Example.

33

1,4-Dihydro-1-(4-methylphenyl)-7-(4-pyridinyl)-4-oxo-3quinolinecarboxamide

[I; R=H, $R^1$=4-CH$_3$C$_6$H$_4$, $R_2$=H, $R_6$=H, $R_7$=4-pyridinyl] was prepared from 3.90 g ethyl 1,4-dihydro-1-(4-methylphenyl)-7-(4-pyridinyl)-4-oxo-3quinolinecarboxylate according to the procedure of Example 32, and was obtained (2.22 g) in the form of its methanesulfonate monohydrate, m.p. above 250° C.(decompn.).

The starting ester, light-tan powder, m.p. 14.5–215.5° C. when recrystallized from ethanol, was prepared according to the procedures of Example 1, substituting 4-methylaniline for the 4-fluoroaniline in part (e) of that Example.

EXAMPLE 34

1,4-Dihydro-1-(2-fluorophenyl)-7-(4-pyridinyl)-4-oxo-3quinolinecarboxamide [I; R=H, $R^1$ =2-FC$_6$H$_4$, $R_2$=H, $R_6$ H, $R_7$ 4-pyridinyl] was prepared from 3.44 g ethyl 1,4-dihydro-1-(2-fluorophenyl)-7-(4-pyridinyl)-4-oxo-3quinolinecarboxylate according to the procedure of Example of 32, and was obtained (1.18 g) in the form of its methanesulfonate salt, pale yellow solid, m.p. above 300° C. when recrystallized from methanol.

The starting ester, m.p. 224–228° C. when recrystalized from ethanol, was prepared according to the procedures of Example 1, substituting 2-fluoroaniline for the 4-fluoroaniline in part (e) of that Example. A sample of said ester was hydrolyzed with potassium carbonate in aqueous ethanol to give 1,4-dihydro-1-(2-fluorophenyl)-7-(4-pyridinyl)-4-oxo-3-quinolinecarboxylic acid, obtained in the form of its hydrochloride salt, m.p. above 300° C.

EXAMPLE 35

1,4-Dihydro-7-(4-pyridinyl)-1-(4-trifluoromethylphenyl)-4-oxo-3-quinolinecarboxamide [I; R=H, $R^1$=4-F$_3$CC$_6$H$_4$, $R_2$=H, $R_6$=H, $R_7$=4-pyridinyl] was prepared from 5.1 g ethyl 1,4-dihydro-7-(4-pyridinyl)-1-(4-trifluoromethyl-phenyl)-4-oxo-3-quinolinecarboxylate according to the procedure of Example 32, and was obtained (2.40 g) in the form of its methanesulfonate salt with 1.5 moles water of hydration, m.p. 270–290° C.

The starting ester, m.p. 192–194° C, was prepared according to the procedures of Example 1, substituting 4-trifluoromethylaniline for the 4-fluoroaniline in part (e) of that Example.

EXAMPLE 36

1-Ethyl-1,4-dihydro-4-oxo-7-phenyl-3-quinolinecarboxylic acid hydrazide [I; R=NH$_2$, $R^1$=C$_2$H$_5$, $R_2$=H, $R_6$=H, $R_7$=C$_6$H$_5$].

A mixture of 3.2 g ethyl 1-ethyl-1,4-dihydro-4-oxo-7-phenyl-3-quinolinecarboxylate (m.p. 127–129° C., prepared by conventional quinolone synthesis starting from 3-phenylaniline and alkylation with ethyl iodide) and 15 ml hydrazine hydrate was heated at 110° C. for 10 min. The reaction mixture was cooled, diluted with 60 ml water, and the solid product was collected, dried and recrystallized from acetonitrile to give 2.25 g product. A further recrystallization from DMF gave 1-ethyl-1,4-dihydro-4-oxo-7-phenyl-3-quinolinecarboxylic acid hydrazide, m.p. 243–244° C.

EXAMPLE 37

(a) Ethyl 7-chloro-1,4-dihydro-1-(4-fluorophenyl)-4-oxo-3quinolinecarboxylate, m.p. 239–241° C., was prepared from ethyl 2,4-dichlorobenzoylacetate, following the reaction sequence of Example 1.

(b) 3-Methyl-5-trimethylstannylthiazole.

A solution of 4.45 g 5-bromo-3-methylthiazole in 50 ml dry ether was cooled to −° C. and treated dropwise over 10 min. with butyllithium (10.5 ml, 26.25 mmol). The mixture was stirred at −° C. for 15 min., and a solution of 5.20 g trimethyltin chloride in 20 ml ether was added dropwise over 10 min. The reaction mixture was allowed to warm to room temperature, stirred overnight, and then washed with water. The ether layer was dried over sodium sulfate, filtered and concentrated in vacuo to give 6.60 g 3-methyl-5-trimethylstannylthiazole as a light-brown liquid used directly in the next reaction.

(c) Ethyl 1,4-dihydro-1-(4-fluorophenyl)-7-(3-methyl-5-thiazolyl)-4-oxo-3-quinolinecarboxylate.

A mixture of 4.34 g ethyl 7-chloro-1,4-dihydro1-(4-fluorophenyl)-4-oxo-3-quinolinecarboxylate, 6.55 g 3-methyl-5-trimethylstannylthiazole and 1.52 g dichlorobis-triphenylphosphine palladium in 150 ml absolute ethanol was heated at 150° C. in a stirred stainless steel bomb for about 16 hrs. The product was isolated and chromatographed on silica gel. Elution with 1:1 ethyl acetate/hexane and 100% ethyl acetate gave 2.67 g ethyl 1,4-dihydro-1-(4-fluorophenyl)-7-(3-methyl-5-thiazolyl)-4- oxo-3-quinolinecarboxylate as a yellow solid.

(d) 1,4-dihydro-1-(4-fluorophenyl)-7-(3-methyl-5-thiazolyl)-4-oxo-3-quinolinecarboxamide [I; R=H, $R^1$=4-FC$_6$H$_4$, $R_2$=H, $R_6$=H, $R_7$=3-methyl-5-thiazolyl] was prepared from 2.67 g ester of part (c) and ammonia according to the procedure of Example 32, and was obtained (0.80 g) as a yellowish-tan powder, m.p. above 221° C. (slow decompn.).

EXAMPLE 38

(a) Dioxobenzoxazine [XII; $R_6$=H, $R_7$=4-pyridinyl].

Phosgene was bubbled for 40 min. through a mixture of 14.0 g 2-amino-4-(4-pyridinyl)benzoic acid and 78 ml 1N potassium hydroxide in 300 ml water. The reaction mixture was purged with nitrogen and filtered. The solid product was stirred with 100 ml water and the pH adjusted to 7.5 with saturated potassium carbonate solution. The product was collected by filtration, dried, and recrystallized from DMF to give 5.07 g of the desired benzoxazine as a light-yellow powder, m.p. 267–271° C.

The starting benzoic acid derivative was prepared from 4-(4-methylphenyl)pyridine by nitration with nitric acid to give 4-(3-nitro-4-methylphenyl)pyridine, oxidation of the latter with potassium permanganate to obtain 2-nitro-4-(4-pyridinyl)benzoic acid and catalytic hydrogenation to form the 2-amino compound.

(b) Ethyl 1-ethyl-1,4-dihydro-2-hydroxy-4-oxo-7-(4-pyridindyl)-3-quinolinecarboxylate.

To a suspension of 0.53 g sodium hydride (50%) in 50 ml DMF was added 2.40 g dioxobenzoxazine from part (a). After 15 min. 1.20 g ethyl bromide was added and the mixture was stirred overnight at room temperature. Sodium hydride (1.06 g) was then added followed by 3.52 g diethyl malonate dropwise. The reaction mixture was heated on a steam bath for 2 hrs., then poured into dilute acetic acid and concentrated in vacuo. The residue was chromatographed on silica gel to give 1.35 g ethyl 1-ethyl-1,4-dihydro-2-hydroxy-4-oxo-7-(4-pyridinyl)-3quinolinecarboxylate used directly in the next reaction. A sample of the compound upon further purification was obtained as a yellow powder, m.p. 153–157° C.

(c) 1-Ethyl-1,2-dihydro-4-hydroxy-2-oxo-7-(4-pyridinyl)-3quinolinecarboxamide [I; R H, $R^1$ =$C_2H_5$, $R_2$ =OH, $R_6$ =H, $R_7$ =4-pyridinyl] was prepared from 0.50 g ester of part (b) and ammonia according to the procedure of Example 31, and was obtained (0.28 g) in the form of its methanesulfonate salt hemihydrate, yellow solid, m.p. 253–256° C. The anhydrous salt had the m.p. 258–260° C.

EXAMPLE 39

(a) Ethyl 1,4-dihydro-2-hydroxy-1-methyl-4-oxo-7-(4-pyridinyl)-3-quinolinecarboxylate was prepared from 7.20 g dioxobenzoxazine of Example 38, part (a), 1.66 g 60% sodium hydride and 1.95 ml methyl iodide according to the procedure of Example 38, part (b), and was obtained (4.50 g) as a yellow solid, m.p. about 184° C(decompn.).

(b) 1,4-Dihydro-2-hydroxy-1-methyl-4-oxo-7-(4-pyridinyl)3-quinolinecarboxamide [I; R=H, $R^1CH_3$, $R_2$ =OH, $R_6$ =H, $R_7$=4-pyridinyl]was prepared from 4.4 g ester of part (a) and ammonia according to the procedure of Example 31, and was obtained (2.56 g) as a light tan powder, m.p. 298–300° C. which recrystallized from DMF.

EXAMPLE 40

(a) 3-cyano-1,4-dihydro-1-ethyl-4-oxo-7-(4-pyri 2-Aminodinyl)quinoline [XIV; $R^1$ =$C_2H_5$, $R_6$ =H, $R_7$ =4-pyridinyl].

To a stirred suspension of 1.09 g 97% sodium hydride in 40 ml DMF at 0° C. under nitrogen was added portionwise 1.45 g malononitrile. After 30 min. there was added 5.37 g compound XIII ($R^1$ =$C_2H_5$, $R_6$ =H, $R_7$ =4-pyridinyl; prepared by alkylation of the dioxobenzoxazine of formula XII (Example 38a) with ethyl iodide), and the reaction mixture was allowed to warm to room temperature and stirred overnight. The reaction mixture was poured into 100 ml 1N hydrochloric acid and the solid product collected and converted to its methanesulfonate salt, giving 5.38 g 2-amino-3-cyano-1,4-dihydro-1-ethyl4-oxo-7-(4-pyridinyl)quinoline methanesulfonate, used directly in the next reaction.

(b) 2-Amino-1,4-dihydro-1-ethyl-4-oxo-7-(4-pyridinyl)-3quinolinecarboxamide [I; R=H, $R^1$ =$C_2H_5$, $R_2$ =$NH_2$, $R_6$ =H, $R_7$ =4-pyridinyl].

A mixture of 2.70 g 2-amino-3-cyano-1,4-dihy- dro-1-ethyl-4-oxo-7-(4-pyridinyl)quinoline methanesulfonate and 25 ml sulfuric acid was heated at 100° C. for 4 hrs. The reaction mixture was cooled, poured onto ice and made basic with ammonium hydroxide. The solid product was collected and recrystallized twice from DMF to give 2.45 g 2-amino-1,4-dihydro-1-ethyl-4-oxo-7-(4-pyridinyl)-3quinolinecarboxamide, m.p. above 300° C.

(a) Ethyl 3,3-di(methylthio)-2-[2-chloro-4-(4-pyridinyl)benzoyl]propenoate.

To a solution of 10.92 g ethyl 2-chloro-4-(4pyridinyl)-benzoylacetate [VII; Alk $C_2H_5$, X'0 Cl, $R_6$=H, $R_7$ 4-pyridinyl in 200 ml THF was added 29.3 g cesium carbonate. The mixture was cooled in an ice bath and 13.3 g carbon disulfide was added. The resulting mixture was stirred for 7 hrs. and 12.8 g methyl iodide was then added. The reaction mixture was stirred overnight at room temperature, then diluted with methylene dichloride, filtered and concentrated in vacuo. The residue was chromatographed to afford 6.56 g yellow oil used directly in the next reaction.

(b) Ethyl 1,4-dihydro-1-(4-fluorophenyl)-2-methylthio-4-oxo-7-(4-pyridinyl)-3-quinolinecarboxylate.

A mixture of 6.00 g crude product of part (a), 1.80 g 4-fluoroaniline and 4.46 g potassium carbonate in 100 ml p-dioxane was stirred 7 hrs. at room temperature and then heated at reflux overnight. The reaction mixture was cooled, diluted with chloroform, filtered and concentrated. The residue was triturated in ether and sonicated to give 3.96 g solid which was purified on silica to give 2.48 g ethyl 1,4-dihydro-1-(4-fluorophenyl)-2-methylthio4-oxo-7-(4-pyridinyl)-3-quinolinecarboxylate.

(c) 2-Amino-1,4-dihydro-1-(4-fluorophenyl)-4-oxo-7-(4-pyriridinyl)-3-quinolinecarboxamide [I; R H, $R^1$ 4-$FC_6H_4$, $R_2$ =$NH_2$, $R_6$ =H, $R_7$ =4-pyridinyl]was prepared by reaction of the product of part (b) with ammonia according to the procedure of Example 31 and was obtained in the form of its methanesulfonate salt hemihydrate, m.p. 294–296° C. (decompn.).

EXAMPLE 42

(a) Ethyl 2-(2,4-Dichlorobenzoyl)-3-(4-fluorophenylamino)propenoate [X; Alk=$C_2H_5$, $R^1$ =4-$FC_6H_4$, $R_6$ =H, X and X'=Cl].

A mixture of 15.67 g ethyl 2,4-dichlorobenzoylacetate, 9.78 g triethyl orthoformate and 24.50 g acetic anhydride was heated at 125° C. for 2 hrs. under nitrogen. The mixture was then cooled to 40° C. and concentrated in vacuo. The residue was dissolved in 50 ml THF and 7.33 g 4-fluoroaniline was added. After 1 hr. the mixture was concentrated in vacuo, and the residue, which crystallized upon scratching and trituration with hexane, was recrystallized from t-butyl methyl ether to give ethyl 2-(2,4- dichlorobenzoyl)-3-(4-fluorophenylamino)propenoate, m.p. 108–111° C.

(b) 1,4-Dihydro-7-chloro-1-(4-fluorophenyl)-4-oxo-3-quinolinecarboxylic acid.

The product of part (a) was cyclized with potassium carbonate to form ethyl 7-chloro-1,4-dihydro-1-(4-fluorophenyl)-4-oxo-3-quinolinecarboxylate (see Example 37a), and the latter hydrolyzed with sodium hydroxide in THF to give 1,4-dihydro-7-chloro-1-(4-fluorophenyl)-4- oxo-3-quinolinecarboxylic acid, m.p. 268–270° C. when recrystallized from acetonitrile.

(c) 1,4-Dihydro-7-chloro-1-(4-fluorophenyl)-4-oxo-3-quinolinecarboxamide [IV; R=H, $R^1$ =4-$FC_6H_4$, $R_2$ =H, $R_6$ =H, X=Cl]was prepared from 2.65 g 1,4-dihydro-7-chloro1-(4-fluorophenyl)-4-oxo-3-quinolinecarboxylic acid by the procedure of Example 1, part (h), and was obtained (1.26 g) in the form of a colorless solid, m.p. 253–255° C when recrystallized from acetonitrile.

(d) 1-(4-Fluorophenyl)-1,4-dihydro-4-oxo-7-(4-pyridinyl)3-quinolinecarboxamide [I; R=H, $R^1$ =4-$FC_6H_4$, $R_2$ =H, $R_6$ =H, $R_7$ =4-pyridinyl}was prepared from 7.92 g 1,4-di- hydro-7-chloro-1-(4-fluorophenyl)-4-oxo-3-quinolinecarboxamide, 7.26 g 4-trimethylstannylpyridine (prepared from 4-bromopyridine hydrochloride and trimethyltin chloride according to the procedure of Example 37, part b) and 0.88 g dichlorobis-triphenylphosphine palladium according to the procedure of Example 37, part (c) and the product recrystallized from DMF to obtain 4.25 g 1-(4-fluorophenyl)-1,4-dihydro-4-oxo-7-(4-pyridinyl)-3-quinolinecarboxamide, the free base corresponding to the compound obtained in Example 1(h).

EXAMPLE 43

(a) 4-Bromo-2-chlorobenzoyl chloride.

A mixture of 4-bromo-2-chlorobenzoic acid (200 g; 0.985 mole) and $PC_{15}$ (225 g; 1.08 moles) was stirred at room temperature for 15 mins. The reaction started with a vigorous evolution of HCl gas and after it subsided, the clear solution was heated on a steam bath for 1 hr. using an efficient gas trap. The reaction mixture was cooled and $POC_{13}$ was removed under an aspirator vacuum (50° C). The residual oil, 221.3 g (94.4%), was used in the next step without further purification.

(b) Ethyl 4-bromo-2-chlorobenzoylacetate [VII; Alk=$C_2H_5$, $R_6$ =H, X=Br, X'=Cl].

A solution of monoethyl malonate (238 g; 1.8 moles) in 1.5 L. of THF and 5 mg of 2,2'-bipyridyl was cooled to -65° C. (Dry Ice-isopropanol) under a nitrogen atmosphere. The n-BuLi (1420 ml; 2.5 M. in hexane) was added at a rate that the temperature did not exceed -10° C. Sufficient n-BuLi was added until a pink color persisted for several minutes The heterogeneous solution was recooled to -65° C. and 4-bromo-2-chlorobenzoyl chloride (214 g; 0.9 mole) in 180 ml of THF was added dropwise over a 30 minute period. The reaction mixture was stirred for another 30 min. at this temperature and then allowed to warm to room temperature (1 hr.). It was quenched into 2.5 L. of cold 1N HCl with vigorous stirring. The stirring was continued for 15 min. and it was then extracted with ethyl acetate (3 x 1 L.). The combined organic layer was washed with two 300 ml portions of saturated sodium bicarbonate, followed by 500 ml of water and dried over anhydrous MgSO4. Removal of the solvent under reduced pressure gave 275 g of the crude product. It was purified by crystallization from hexane at 0° C. and two crops were collected to give essentially pure product 210 g (77%).

(c) Ethyl 3-(4-fluoroanilino)-2-(4-bromo-2-chlorobenzoyl)propenoate [X; Alk=$C_2H_5$, $R^1$ =4-$FC_6H_4$, $R_6$ =H, X=Br, X'=Cl].

A solution of ethyl 4-bromo-2-chlorobenzoylacetate (300 g; 0.99 mole) and dimethylformamide dimethylacetal (123 g; 1 mole) in 600 ml of THF was stirred at room temperature for 22 hours. At the end of this period, the reaction mixture was cooled to 0-5° C. and 4-fluoroaniline (114 g; 1 mole) in 70 ml of THF was added dropwise over a 30 minute period. After the addition was complete, it was stirred at this temperature for one hour and then the solvent was removed under reduced pressure to give an orange oil in quantitative recovery. This crude product was used without further purification in the next step.

(d) Ethyl 7-bromo-1-(4-fluorophenyl)-1,4-dihydro-4-oxo3-quinolinecarboxylate.

A suspension of ethyl 3-(4-fluoroanilino)-2(4-bromo-2-chlorobenzoyl)propenoate (420 g; 0.986 mole) and milled potassium carbonate (165 g; 1.2 moles) in 700 ml of DMF was heated to 150° C. for 1.5 hours. The reaction mixture was cooled and poured into 7.5 L. of ice-water. The yellow solid was filtered, washed with 1 L. of water and ethanol until an off-white product was obtained. It was then dried in an oven at 70° C. for 18 hrs. to give 304 g (79%) of pure quinolone ester, m.p. 268-270° C.

(e) 7-Bromo-1-(4-fluorophenyl)-1,4-dihydro-4-oxo-3-quinolinecarboxylic acid.

A solution of ethyl 7-bromo-1-(4-fluorophenyl)1,4-dihydro-4-oxoquinolinecarboxylate (100 g; 0.256 mole), 400 ml of 1N NaOH and 700 ml of THF was refluxed for 2.5 hrs. It was cooled, THF was removed by distillation and the residue cooled to 0-5° C. It was acidified with 2N HCl, the white solid filtered and washed with 1.5 L. of water The product was dried in an oven at 70° C. for 18 hrs. to give 90.4 g (97.5%) of quinolinecarboxylic acid. This product was used in the next step without further purification.

(f) 7-Bromo-1-(4-fluorophenyl)-1,4-dihydro-4-oxo-3-quinolinecarboxamide [IV; R=H, $R^1$ =4-$FC_6H_4$, $R_2$ =H, $R_6$ H, X=Br].

To a solution of 7-bromo-1-(4-fluorophenyl)1,4-dihydro-4-oxo-3-quinolinecarboxylic acid (198.3 g; 0.55 mole) in 850 ml of DMF was added 1,1'-dicarbonylimidazole (132.7 g; 0.85 mole) and the mixture was heated on a steam bath for 2.5 hrs. It was then cooled to 0-5° C and anhydrous ammonia was bubbled through the solution for 30 min. It was allowed to warm to room temperature (1 hr.) and diluted with 3 L. of water. The yellowish solid was filtered and washed sequentially with 1 L. of water and 1 L. of ethanol to give a white solid. It was dried in an oven at 70° C. for 25 hrs. and gave 191.3 g (96.3%) of the quinolinecarboxamide which was used in the next step without purification.

(g) 4-Tributylstannylpyridine.

To a suspension of 4-bromopyridine hydrochloride (150 g; 0.773 mole) in 1.2 L. of dry ether at 0-5° C. was added 500 ml cold saturated solution of $NaHC_{03}$ over a 30 min, period. After the addition was complete, it was stirred at 0-5° C. for 15 min., the organic layer was separated and dried over anhydrous $K_2CO_3$. The organic layer was filtered, washed with 200 ml of ether and the filtrate was cooled to −60° C. (Dry Ice/ether) under a nitrogen atmosphere. To this stirred solution was added n-BuLi (2.5 M; 300 ml in hexane) dropwise over a one hour period. The temperature was maintained at about −60° C. throughout the addition. After the addition was complete, it was stirred for 15 min. and tributyltin chloride (238 g; 0.732 mole) was added dropwise over 45 min. Since tin compounds are very toxic, all operations were carried out inside the hood and with a respirator. The temperature during the addition did not exceed −56° C. and the reaction mixture was allowed to stir at −60° C. for 30 min. The Dry Ice bath was removed and the reaction mixture was warmed to room temperature (1.5 hr.). The inorganic salts were filtered off through a bed of supercel and washed with 400 ml of ether. The filtrate was concentrated on a steam-bath to remove the solvent. At the end, a water aspirator was used to completely remove n-butylbromide. The residual product 246 g (92%) was purified by Kugelrohr distillation. The product distilling at 110-120° C. (0.1 mm Hg) was collected as a colorless oil, 205 g, (73% yield).

(h) 1-(4-Fluorophenyl)-1,4-dihydro-4-oxo-7-(4-pyridinyl)3-quinolinecarboxamide monomethanesulfonate hemihydrate [I; R=H, $R^1$ =4-$FC_6H_4$, $R_2$ =H, $R_6$ =H, $R_7$ =4-pyridinyl].

A mixture of 7-bromo-1-(4-fluorophenyl)-1,4- dihydro-4-oxo-3-quinolinecarboxamide (85 g; 0.235 mole), 4-tributylstannylpyridine (115 g; 0.313 mole) and dichlorobis(triphenylphosphine) palladium (8 g; 5 molar %) in 20 ml DMF under a nitrogen atmosphere was slowly heated to 155-160° C. and held at that temperature for five hours. The mixture was cooled to room temperature and stirred with 500 ml of ether and the crude product (black solid) was filtered, washed with 200 ml of ether and air dried to give 76 g (91% recovery). This crude product was suspended in 1200 ml of EtOH:H$_2$O (80:20) and heated to 75-80° C. on a steam bath. Methanesulfonic acid (27 g; 0.282 mole) was added dropwise to the above stirred solution over 10 min. and the insoluble inorganic salts along with non-basic impurities were filtered off. After cooling the filtrate to 0-5° C. for 30 min., the crystalline product was filtered and washed with 50 ml cold EtOH:H$_2$O (80:20). It was dried at 70° C. under vacuum for 18 hrs. to give 56 g (51%) of pure compound, identical with that obtained in Example 1(h).

EXAMPLE 44

1,4-Dihydro-1-(4-fluorophenyl)-4-oxo-7-phenyl-3-quinolinecarboxamide [I; R=H, R$^1$=4-FC$_6$H$_4$, R$_2$=H, R$_6$=H, R$_7$C$_6$H$_5$] was prepared from 2.22 g 1,4-dihydro-7-chloro1-(4-fluorophenyl)-4-oxo-3-quinolinecarboxamide (Example 42c), 3.30 g tributylstannylbenzene (prepared from tributyltin chloride and bromobenzene) and 2.50 g dichlorobis-triphenylphosphine palladium according to the procedure of Example 37, part (c), and was obtained (1.4 g) as colorless crystals, m.p. 289-292° C. when recrystallized from acetonitrile.

EXAMPLE 45

(a) Ethyl 2-(2,4-dichlorobenzoyl)-3-phenylamino-propenoate [X; Alk=C$_2$H$_5$, R$^1$=C$_6$H$_5$, R$_6$=H, X and X'=Cl] was prepared according to the procedure of Example 42(a), replacing the 4-fluoroaniline of that example by aniline, and was obtained as a viscous orange oil used directly in the next reaction.

(b) Ethyl 7-chloro-1,4-dihydro-4-oxo-1-phenyl-3-quinolinecarboxylate.

To a solution of the product of part (a) (9.74 g) in 250 ml THF under nitrogen was added portionwise 1.18 g 60% sodium hydride. The reaction mixture was stirred overnight and then concentrated in vacuo. The residue was partitioned between methylene dichloride and 1N HCl solution. The organic layer was dried (MgSO4) and concentrated to give 7.36 g solid used directly in the next reaction.

(c) 7-Chloro-1,4-dihydro-4-oxo-1-phenyl-3-quinolinecarboxylic acid was prepared by hydrolysis of the ester of part (b) with sodium hydroxide in THF at 100° C. for 1 hr., and was obtained as a colorless solid, m.p. 283-286° C (decompn.) when recrystallized from DMF.

(d) 7-Chloro-1,4-dihydro-4-oxo-1-phenyl-3-quinolinecarboxamide [IV; R=H, R$^1$=C$_6$H$_5$, R$_2$=H, R$_6$=H, X=Cl] was prepared from 3.60 g 7-chloro-1,4-dihydro-4-oxo-1-phenyl3-quinolinecarboxylic acid by the procedure of Example 1, part (h), and was obtained (3.00 g) in the form of a colorless solid, m.p. 297-299° C. when recrystallized from DMF.

(e) 1,4-Dihydro-4-oxo-1-phenyl-7-(4-pyridinyl)-3-quinolinecarboxamide [I; R=H, R$^1$=C$_6$H$_5$, R$_2$=H, R$_6$=H, R$_7$=4-pyridinyl] was prepared from 5.39 g 7-chloro-1,4-di- hydro-4-oxo-1-phenyl-3-quinolinecarboxamide, 5.32 g 4-trimethylstannylpyridine and 0.63 g dichloro-bis-triphenylphosphine palladium according to the procedure of Example 37, part (c), and was obtained (3.83 g) in the form of its methanesulfonate salt hemihydrate, light-yellow powder, m.p. above 310° C. when recrystallized from aqueous ethanol Example 46 a) Ethyl 2-(2,4-dichlorobenzoyl)-3-(3-fluorophenylamino)propenoate [X; Alk=C$_2$H$_5$, R$^1$=3-FC$_6$H$_4$, R$_6$=H, X and X'0 Cl] was prepared according to the procedure of Example 42(d), replacing the 4-fluoroaniline of that example by 3-fluoroaniline, and was obtained as a colorless solid, m.p. 107-109° C. b) Ethyl 7-chloro-1,4-dihydro-1-(3-fluorophenyl)-4-oxo-3quinolinecarboxylate was prepared from 19.53 g ethyl 2-(2,4-dichlorobenzoyl)-3-(3-fluorophenylamino)-propenoate and 10.50 g potassium carbonate in refluxing dioxane and was obtained (13.29 g) as a colorless solid, m.p. 268270° C. when recrystallized from acetonitrile.

(c) 7-Chloro-1,4-dihydro-1-(3-fluorophenyl)-4-oxo-3-quinolinecarboxylic acid was prepared by hydrolysis of the ester of part (b) with sodium hydroxide in THF at 100° C for 1 hr., and was obtained in 80% yield as a colorless solid, m.p. 284-286° C. when recrystallized from acetonitrile.

(d) 7-Chloro-1,4-dihydro-1-(3-fluorophenyl)-4-oxo-3-quinolinecarboxamide [IV; R=H, R$^1$=3-FC$_6$H$_4$, R$_2$=H, R$_6$ H, X=Cl] was prepared from 7.36 g 7-chloro-1,4-dihydro1-(3-fluorophenyl)-4-oxo-3-quinolinecarboxylic acid by the procedure of Example 1, part (h), and was obtained (7.14 g) as a colorless solid, m.p. 294-296° C. when recrystallized from DMF. e) 1,4-Dihydro-1-(3-fluorophenyl)-4-oxo-7-(4-pyridinyl)3-quinolinecarboxamide [I; R=H, R$^1$=3-FC$_6$H$_4$, R$_2$=H, R$_6$ H, R$_7$ 4-pyridinyl] was prepared from 4.13 g 7-chloro-1,4-dihydro-1-(3-fluorophenyl)-4-oxo-3-quinolinecarboxamide, 3.78 g 4-trimethylstannylpyridine and 0.46 g dichloro-bis-triphenylphosphine palladium according to the procedure of Example 37, part (c), and was obtained (2.4 g) in the form of its methanesulfonate salt, m.p. above 320° C. when recrystallized from methanol.

EXAMPLE 47

(a) Ethyl 3,3-di(methylthio)-2-(4-bromo-2-chlorobenzoyl)propenoate was prepared from ethyl 4-bromo-2-chlorobenzoylacetate (Example 43b) according to the procedure of Example 41(a). The resulting amber oil, obtained in 28% yield was used directly in the next reaction.

(b) Ethyl 7-bromo-1,4-dihydro-1-(4-fluorophenyl)-2-methyl- thio-4-oxo-3-quinolinecarboxylate was prepared from the product of part (a), 4-fluoroaniline and potassium carbonate according to the procedure of Example 41(b), and was obtained in 45% yield as beige colored crystals. c) Ethyl 7-bromo-2-hydroxy-1-(4-fluorophenyl)-1,4-dihy- dro-4-oxo-3-quinolinecarboxylate.

The product of part (b) (3.41 g) and 8.5 ml 1N potassium hydroxide in 50 ml THF was heated at reflux for about 16 hrs. The reaction mixture was concentrated in vacuo and the residue partitioned between 1N hydrochloric acid and methylene dichloride. The organic portion was concentrated to give an oily residue containing a mixture of product and starting material. The latter was heated with an additional 5 ml 1N KOH in THF and the product isolated to give 3.13 g ethyl 7-bromo-2-hydroxy-1-(4- fluorophenyl)-1,4-dihydro-4-oxo-3-quinolinecarboxylate in crude form used directly in the next reaction.

(d) 7-Bromo-2-hydroxy-1-(4-fluorophenyl)-1,4-dihydro-4- oxo-3-quinolinecarboxamide [IV; R H, R$^1$=4-FC$_6$H$_4$, R$_2$=OH, R$_6$=H, X=Br] was prepared from the product of part (c) (0.45 g) and ammonia according to the procedure of Example 31, and was obtained (0.28 g) in the form of a colorless powder used directly in the next reaction.

(e) 1,4-Dihydro-1-(4-fluorophenyl)-2-hydroxy-7-(4-pyridinyl)4-oxo-3-quinolinecarboxamide I; R=H, R$^1$=4-FC$_6$H$_4$, R$_2$=OH, R$_6$=H, R$_7$=4-pyridinyl] was prepared from the product of part (d) (0.28 g), 0.20 g 4-trimethylstannylpyridine and 0.026 g dichloro-bis-triphenylphosphine palladium according to the procedure of Example 37, part (c), and was obtained (0.117 g) in the form of its methanesulfonate dihydrate, pale-yellow solid, m.p. 275278° C.(decompn.).

EXAMPLE 48

(a) Ethyl 1,4-dihydro-6-fluoro-1-(4-fluorophenyl)-4-oxo-7(4-pyridinyl)-3-quinolinecarboxylate III; loweralkyl=$C_2H_5$, $R^1$ =4-$FC_6H_4$, $R_2$ =H, $R_6$ =F, $R_7$ =4-pyridinyl]was prepared from 3.50 g 7-chloro-1,4-dihydro-6-fluoro-1(4-fluorophenyl)-4-oxo-3-quinolinecarboxylic acid ester J. Med. Chem. 28, 1558 (1985)]according to the procedure of Example 37, part (c), and was obtained (0.64 g) in the form of a colorless solid, m.p. 242.5° C. b) 7-Chloro-1,4-dihydro-6-fluoro-1-(4-fluorophenyl)-4- oxo-3-quinolinecarboxamide [IV; R H, $R^1$ =4-$FC_6H_4$, $R_2$ H, $R_6$ F, X Cl]was prepared from 2.1 g methyl 7-chloro-1,4-dihydro-6-fluoro-1-(4-fluorophenyl)-4-oxo-3quinolinecarboxylate according to the procedure of Example 31, and was obtained (1.90 g) in the form of a pale-yellow powder used directly in the next reaction (c) ],4-Dihydro-6-fluoro-1-(4-fluorophenyl)-4-oxo-7-(4- pyridinyl)-3-quinolinecarboxamide [I; R=H, $R^1$ =4-$FC_6H_4$, $R_2$ =H, $R_6$ =F, $R_7$ =4-pyridinyl]was prepared from the product of part (b) (1.95 g) according to the procedure of Example 37, part (c), and was obtained (0.61 g) in the form of a colorless solid, m.p. above 300° C. when recrystallized from methanol.

The antiviral properties of the compounds of the invention were evaluated by the following procedures:

In Vitro - Plaque Reduction Assay in Vero Cells

The tissue cultures were prepared as follows: Two-day old, confluent cell monolayers were used. Six-well Costar plates were seeded at a cell density of $1.2 \times 10^6$ Vero (African Green Monkey Kidney) cells per well in growth media (Hank's minimum essential medium containing 5% inactivated fetal calf serum). Plates were maintained in a 37° humidified incubator with 2.0% $C_{02}$ in air until use. Overlay media were prepared by making a 1:150 dilution of human immune serum Globulin into M199 media containing 5% inactivated newborn calf serum. A 1:200 dilution of each level of test compound (35 μl) (prepared in dimethylsulfoxide or sterile water) was made in 7 ml overlay media. DMSO or $H_{20}$ was used in place of test compound in tissue culture and virus control overlays Maintenance media were aspirated from plates and 1 ml of herpes simplex virus type 2 (Curtis strain), containing 85 pfu in M199 media, was dispensed into each well. After 1 hour incubation at 37° C. 2% $C_{02}$, virus was aspirated and 3 ml of compound overlay added to each well-2 wells per level of compound. After plates were overlayed, they were incubated at 37° C. 2% $C_{02}$ for 3 days.

Plates were fixed by adding approximately 2 ml of a 5% (v/v) glutaraldehyde/$H_{20}$ fixative to each well and allowing plates to sit at room temperature for at least 1 hour. Plates were then rinsed in $H_{20}$ and stained by the addition of 0.25% crystal violet stain (2.5 gms of crystal violet per liter $H_{20}$) and allowed to sit for 10 minutes Plates were rinsed in $H_{20}$ and allowed to air dry. Plaques were easily visualized and counted using the Model 982 Artek Counter with Model 890 light box. The effective dose 50% (ED50) for a compound was defined as the concentration which inhibits plaque formation by 50%.

In Vivo - Intravaginal Herpes Virus Infection in Mice

Approximately 1 hr. prior to infection, the vaginas of 15 gm albino mice were swabbed with cotton saturated with 0.1 N NaOH to remove vaginal secretions and to irritate the vaginal mucosa slightly. At the proper time, 0.05 ml of an appropriate dose of herpes simplex virus was placed deep in the vagina. Starting 2.5 hrs. prior to infection, the mice were medicated either orally or intraperitoneally. Medication was continued daily for a total of 5 days on a b.i.d. regimen. The test was terminated after 14 days. A comparison of the number of surviving mice and/or extension of survival was made at the end of the test. The criterion for activity was a statistically significant extension of the average survival time of the test group over that of the control mice in two experiments.

The results of the testing on the compounds of the invention are given in the following table;

| Example No. | In Vitro MIC | In Vitro MTL | In Vivo MED | In Vivo MTL |
|---|---|---|---|---|
| 1h, 43 | 0.21-0.24 | >3.1 | 12.5-25 | 50-100 |
| 2 | NA | >12.5 | 25 | 100 |
| 3 | 0.28 | 12.5 | 50 | 100 |
| 4 | 5.8 | >12.5 | NT | |
| 5 | 1.1 | >12.5 | NT | |
| 6 | 6.5 | 12.5 | 50 | 50 |
| 7 | 9.9 | 12.5 | NA | 25 |
| 8 | 1.3 | >25 | NA | 50 |
| 9 | NA | >25 | NT | |
| 10 | 7.2 | >200 | 50-75 | 75 (QNS) |
| 11 | 4.0 | 25 | NA | 25 |
| 12 | 1.7 | >100 | NA | >100 |
| 13 | 1.0 | >100 | NA | |
| 14 | 0.52 | >12.5 | 50 | 100 |
| 15 | 2.2 | 3.1 | NA | <25 |
| 16 | 4.6 | >25 | NA | 25 |
| 17 | 5.2 | 6.2 | NA | 50 |
| 18 | NA | 6.25 | NT | |
| 19 | 2.9 | 6.25 | NA | <50 |
| 20 | 14 | 25 | NA | 100 |
| 21 | 0.64 | 6.25 | QNS | |
| 22f | 0.26 | >100 | NA | >200 |
| 23d | 12.5 | >100 | NA | >200 |
| 24c | 5.0 | 12.5 | NA | >200 |
| 25 | NA | >100 | T | |
| 26 | 4.8 | 6.2 | NA | 50 |
| 27b | 12 | 50 | NA | 100 |
| 28 | 9.0 | >25 | 50 | 50 |
| 29 | 38 | 50 | NA | 100 |
| 30 | 6.8 | 25 | NA | 100 |
| 31 | 0.47 | >12.5 | 50 | 50 |
| 32 | 0.40 | >25 | 50 | 100 |
| 33 | 0.63 | >25 | NA | 50 |
| 34 | NA | 1.6 | NA | 100 |
| 35 | 1.0 | >100 | NA | 50 |
| 36 | 13 | 25 | NA | >200 |
| 37d | 0.25 | >100 | NA | >100 |
| 38c | 7.7 | >12.5 | 100-200 | 100 |
| 39b | 2.1 | 3.1 | 150-200 | 150 |
| 40b | 9.0 | >12.5 | NA | >100 |
| 41c | 0.33 | >100 | 50 | 100 |
| 44 | 0.82 | 12.5 | NA | >200 |
| 45e | 0.78 | >6.25 | 25 | 50 |
| 46e | 0.71 | >6.25 | 25-50 | 50 |
| 47e | 10.7 | >100 | QNS | |
| 48c | 1.5 | 6.25 | NA | >100 |

MIC = Minimum inhibitory concentration (μg/ml)
MTL = Maximum tolerated dose
MED = Minimum effective dose (mg/kg/day)
NA = Not active at dose levels tested
QNS = Insufficient sample
NT = Not tested The antiviral compositions are formulated for use by preparing a dilute solution or suspension in a pharmaceutically acceptable aqueous, organic or aqueousorganic medium for topical or parenteral administration by intravenous or intramuscular injection, or for intranasal or ophthalmic application; or are prepared in tablet, capsule, or aqueous suspension form with conventional excipients for oral administration.

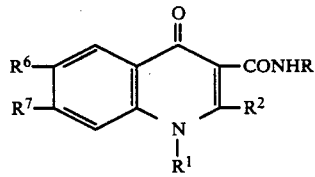

I claim:
1. A compound of the formula

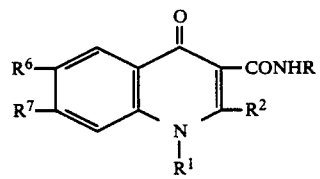

wherein
R is hydrogen, hydroxy, amino, lower-alkyl or $CH_2N=Z$, wherein $N=Z$ is di-lower-alkylamino, 1-pyrrolidyl, 1-piperidinyl or 4-morpholinyl; $R^1$ is lower-alkyl, lower-alkenyl, cycloalkyl, pyridinyl, or phenyl or phenylmethyl where phenyl can be substituted by from one to three substituents selected from halo, lower-alkyl, lower-alkoxy and trifluoromethyl;
$R_2$ is hydrogen, amino or hydroxy;
$R_6$ is hydrogen or fluoro; and
$R_7$ is pyridinyl, pyridinyl substituted by one or two lower-alkyl groups, pyridinyl-N-oxide, phenyl, 5-isoxazolyl, 3-methyl-5-isoxazolyl or 3-methyl5-thiazolyl, with the proviso that when R is hydrogen or lower-alkyl, $R^1$ is lower-alkyl and $R_7$ is phenyl, $R_2$ is other than hydrogen;
or a pharmaceutically acceptable acid-addition salt thereof.

2. A compound according to claim 1, wherein R, $R_2$ and $R_6$ are hydrogen, and $R_7$ is pyridinyl.

3. 1-Ethyl-1,4-dihydro-4-oxo-7-(4-pyridinyl)-3quinolinecarboxamide, according to claim 2.

4. A compound according to claim 2, wherein $R^1$ is phenyl or substituted phenyl.

5. 1-(4-Fluorophenyl)-1,4-dihydro-4-oxo-7-(4-pyridinyl)-3-quinolinecarboxamide, according to claim 4.

6. A compound according to claim 1, wherein $R_2$ is amino.

7. 2-Amino-1,4-dihydro-1-(4-fluorophenyl)-7-(4-pyridinyl)-4-oxo-3-quinolinecarboxamide, according to claim 6.

8. A composition for combating herpes viruses, which comprises an antivirally effective amount of a compound according to claim 1 together with one or more pharmaceutically acceptable excipients or diluents.

9. A composition according to claim 8 wherein the compound is 1-(4-fluorophenyl)-1,4-dihydro-4-oxo-7(4-pyridinyl)-3-quinolinecarboxamide or a pharmaceutically acceptable salt thereof.

10. A method for combating herpes viruses, which comprises contacting the locus of said viruses with a composition according to claim 8.

11. A method for combating a herpes virus infection in a mammalian host which comprises administering to said host an antivirally effective amount of a composition according to claim 8.

12. A method for combating a herpes virus infection in a mammalian host which comprises administering to said host an antivirally effective amount of a composition according to claim 9.

* * * * *